(12) United States Patent
Masuda

(10) Patent No.: US 7,799,045 B2
(45) Date of Patent: Sep. 21, 2010

(54) TREATMENT APPARATUS AND TREATMENT DEVICE FOR SURGICAL TREATMENTS USING ULTRASONIC VIBRATION

(75) Inventor: Shinya Masuda, Yokohama (JP)

(73) Assignee: Olympus Corporation (JP)

( * ) Notice: Subject to any disclaimer, the term of this patent is extended or adjusted under 35 U.S.C. 154(b) by 1074 days.

(21) Appl. No.: 11/093,601

(22) Filed: Mar. 30, 2005

(65) Prior Publication Data

US 2005/0234338 A1 Oct. 20, 2005

(30) Foreign Application Priority Data

Mar. 30, 2004 (JP) ............................. 2004-098229

(51) Int. Cl.
*A61B 17/32* (2006.01)
*A61B 18/18* (2006.01)

(52) U.S. Cl. ........................................ 606/169; 606/37

(58) Field of Classification Search ................. 600/439; 601/2, 3; 606/169
See application file for complete search history.

(56) References Cited

U.S. PATENT DOCUMENTS

| | | | |
|---|---|---|---|
| 5,176,677 A * | 1/1993 | Wuchinich | 606/46 |
| 5,322,055 A * | 6/1994 | Davison et al. | 601/2 |
| 5,603,723 A * | 2/1997 | Aranyi et al. | 606/205 |
| 5,628,743 A * | 5/1997 | Cimino | 606/1 |
| 5,637,110 A * | 6/1997 | Pennybacker et al. | 606/46 |
| 5,836,897 A * | 11/1998 | Sakurai et al. | 601/2 |
| 5,906,628 A * | 5/1999 | Miyawaki et al. | 606/169 |
| 6,015,415 A * | 1/2000 | Avellanet | 606/113 |
| 6,017,358 A * | 1/2000 | Yoon et al. | 606/205 |
| 6,024,750 A * | 2/2000 | Mastri et al. | 606/169 |
| 6,129,735 A * | 10/2000 | Okada et al. | 606/169 |
| 6,206,844 B1 * | 3/2001 | Reichel et al. | 601/2 |
| 6,214,023 B1 * | 4/2001 | Whipple et al. | 606/169 |
| 6,340,352 B1 * | 1/2002 | Okada et al. | 601/2 |
| 6,371,956 B1 * | 4/2002 | Wilson et al. | 606/49 |
| 6,454,782 B1 * | 9/2002 | Schwemberger | 606/174 |
| 6,569,178 B1 * | 5/2003 | Miyawaki et al. | 606/169 |
| 6,585,735 B1 * | 7/2003 | Frazier et al. | 606/51 |
| 6,682,544 B2 * | 1/2004 | Mastri et al. | 606/169 |
| 6,790,216 B1 * | 9/2004 | Ishikawa | 606/169 |

(Continued)

FOREIGN PATENT DOCUMENTS

JP 2002-224133 8/2002

(Continued)

*Primary Examiner*—Long V Le
*Assistant Examiner*—Angela M Hoffa
(74) *Attorney, Agent, or Firm*—Ostrolenk Faber LLP

(57) ABSTRACT

An ultrasonic treatment device comprises a transducer unit, probe unit, and a main unit. The transducer unit comprises an ultrasonic transducer generating ultrasonic vibration in response to supply of power. The probe unit has a treatment member at a distal end thereof. The probe unit is detachably loaded to the transducer unit, and is equipped with an ultrasonic probe transmitting the ultrasonic vibration to the distal end of the treatment member when the transducer unit is loaded to the probe unit. The main unit is manually grasped by an operator. The probe unit with the transducer unit loaded thereto is detachably loaded to the main unit. The main unit has a cylindrical insert through which the ultrasonic probe is inserted to have the treatment member protruded outwardly when the probe unit is loaded. The main unit further has an outer sheath detachably covering an outer surface of the insert.

18 Claims, 18 Drawing Sheets

U.S. PATENT DOCUMENTS

| | | | |
|---|---|---|---|
| 6,887,252 B1* | 5/2005 | Okada et al. | 606/169 |
| 6,893,434 B2* | 5/2005 | Fenton et al. | 606/37 |
| 6,918,906 B2* | 7/2005 | Long | 606/41 |
| 7,052,506 B2* | 5/2006 | Young et al. | 606/169 |
| 7,083,618 B2* | 8/2006 | Couture et al. | 606/51 |
| 7,264,618 B2* | 9/2007 | Murakami et al. | 606/27 |
| 7,306,599 B2* | 12/2007 | Karasawa et al. | 606/51 |
| 2002/0147447 A1* | 10/2002 | Long | 606/41 |
| 2002/0177373 A1* | 11/2002 | Shibata et al. | 439/894 |
| 2002/0183739 A1* | 12/2002 | Long | 606/41 |
| 2002/0188294 A1* | 12/2002 | Couture et al. | 606/51 |
| 2003/0135136 A1* | 7/2003 | Murakami | 601/2 |
| 2004/0186463 A1* | 9/2004 | Murakami et al. | 606/27 |
| 2005/0004589 A1* | 1/2005 | Okada et al. | 606/169 |
| 2005/0021017 A1* | 1/2005 | Karasawa et al. | 606/28 |
| 2006/0241532 A1* | 10/2006 | Murakami | 601/2 |

FOREIGN PATENT DOCUMENTS

JP  2004-283361  10/2004

* cited by examiner

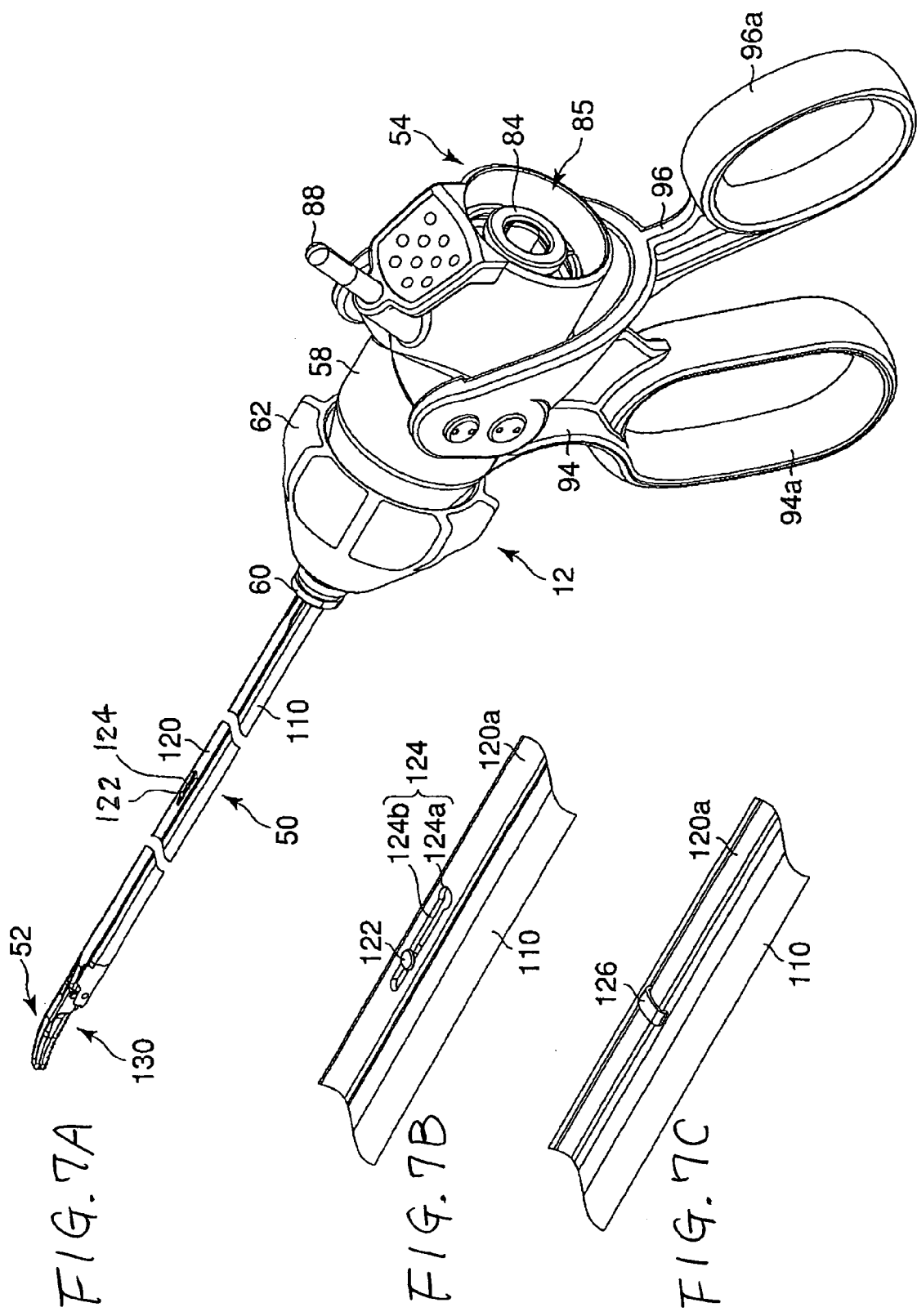

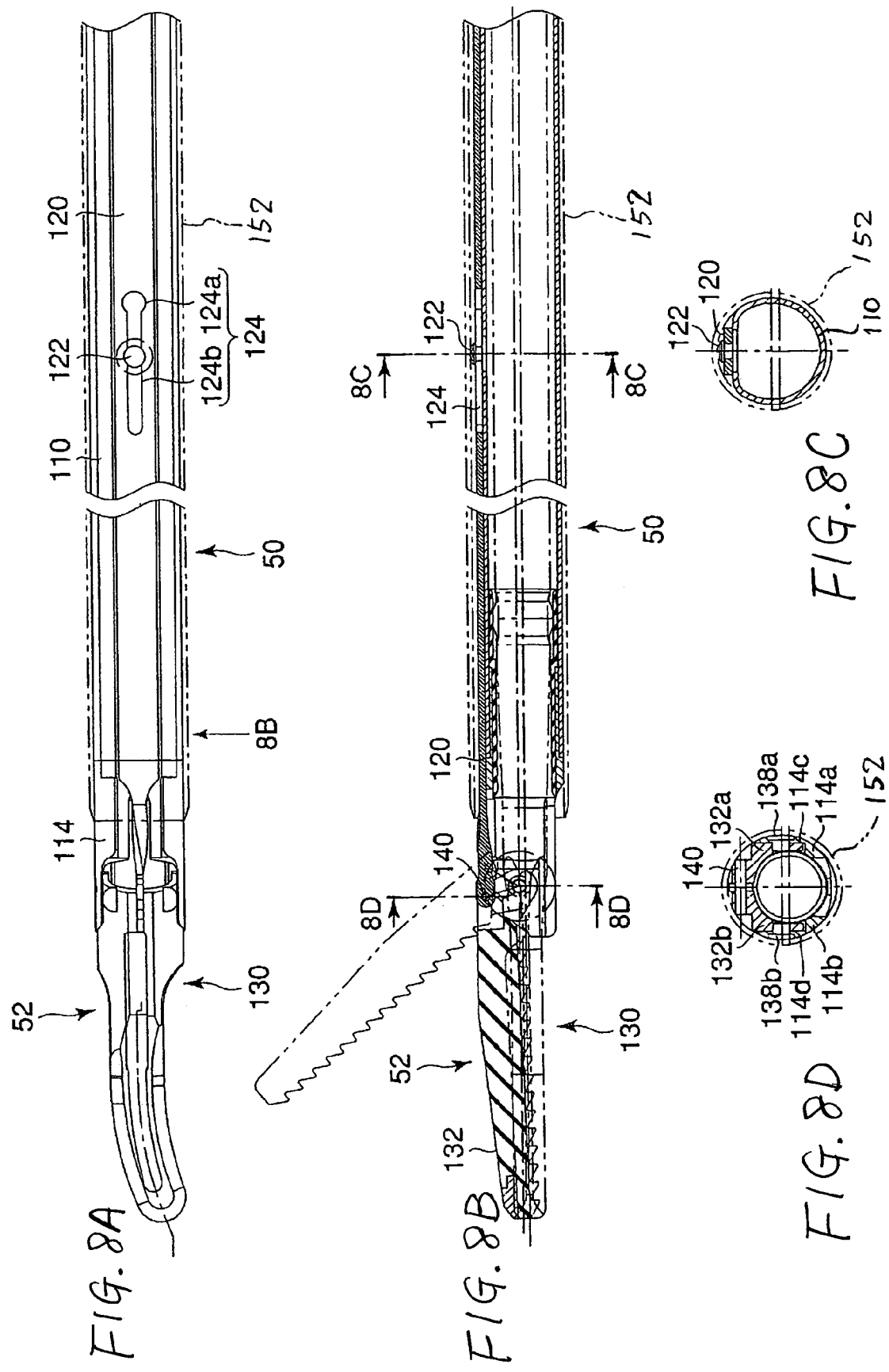

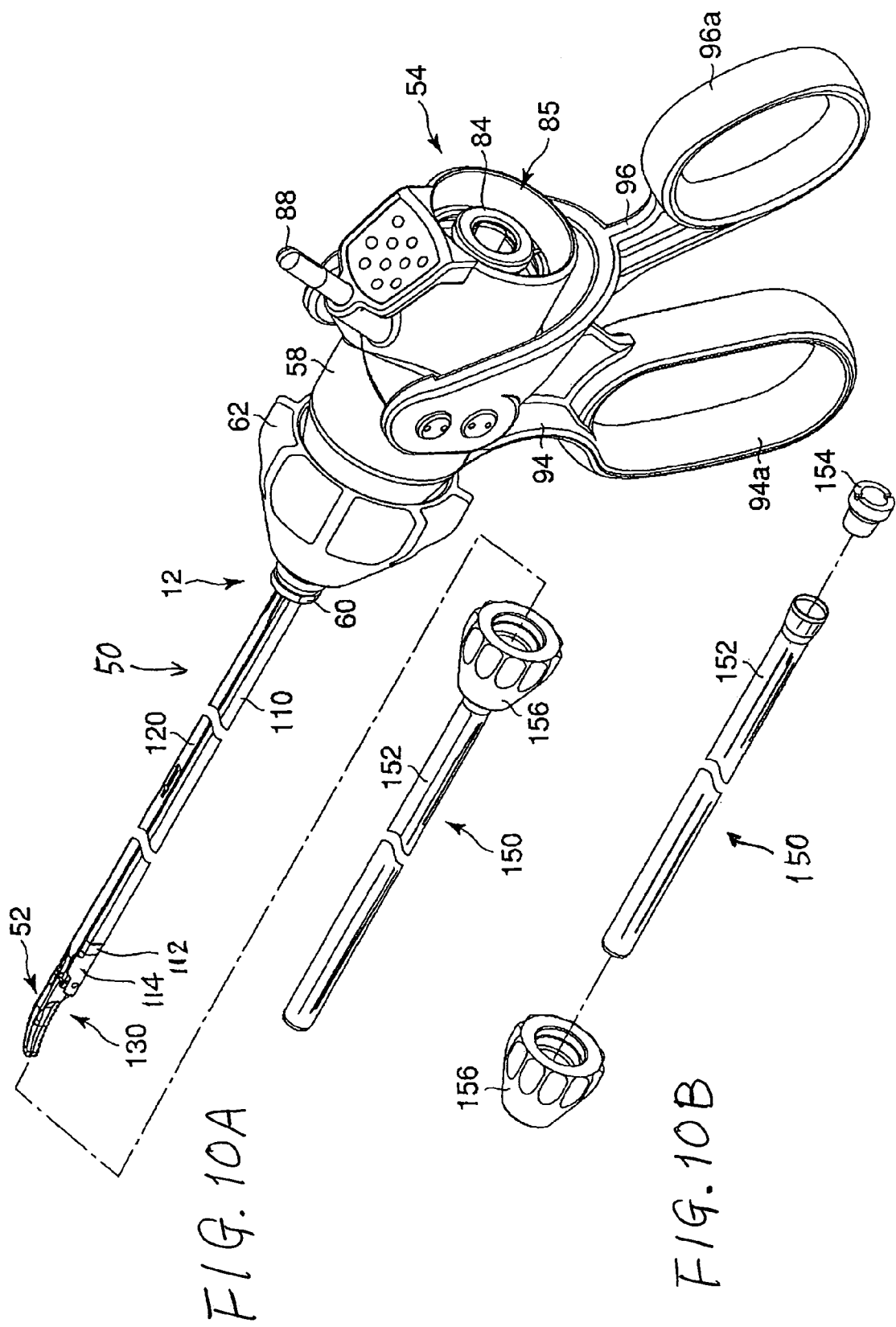

TREATMENT APPARATUS AND TREATMENT DEVICE FOR SURGICAL TREATMENTS USING ULTRASONIC VIBRATION

CROSS REFERENCE TO RELATED APPLICATION

The present application relates to and incorporates by reference to Japanese Patent Application No. 2004-098229 filed on Mar. 30, 2004.

BACKGROUND OF THE INVENTION

1. Technical Field

The present invention relates to an ultrasonic treatment device and an ultrasonic treatment apparatus that are able to generate ultrasonic vibration for enabling treatment on a living tissue using such ultrasonic vibration.

2. Related Art

Now, ultrasonic treatment apparatuses have become a vital requirement as one of medical devices in medical wards for surgeries.

The ultrasonic treatment apparatuses include those of various types as described below. Such examples include one that is known from Japanese Patent Provisional Publication No. 2002-224133. This literature discloses an ultrasonic treatment device in which ultrasonic vibration, generated with an ultrasonic transducer, is transmitted to a probe to allow a treatment member, mounted onto a distal end of the probe, to execute a treatment on a living tissue utilizing the ultrasonic vibration. The ultrasonic treatment device is comprised of a main unit, a probe unit and a transducer unit, all of which are mounted to be detachable from among three component parts.

Among these, the main unit is comprised of an operational main part, an inner sheath to which a vibration transmitting member is inserted when the probe unit is fitted to the operational main part, a jaw located on a distal end of the inner sheath in face-to-face relationship with a distal end of the vibration transmitting member, an operational force transfer member for rotating the jaw that operates an operating portion disposed on the operational main part, and an outer sheath by which the operational force transfer member and the inner sheath are covered. The operational main part, the inner sheath, the outer sheath and the operational force transfer member, which are formed in a substantially integrated fashion.

With such a case of the ultrasonic treatment device, the probe unit and the transducer unit are separated from the main unit, after use, for cleaning various units. For example, in cases where filths, such as blood or the like, intrude a space between the inner sheath and the outer sheath of the main unit, using implements, such as special cleaning device and a syringe or the like, causes a cleaning liquid to burst into the space between the inner sheath and the outer sheath, thereby letting out the filths from between the inner sheath and the outer sheath for cleaning.

Since the main unit of the ultrasonic treatment device, disclosed in the above patent literature, is formed in the substantially integrated fashion, it takes time when cleaning the inner sheath, the outer sheath and the operational force transfer member. For instance, when removing the filths, intruded to between the inner sheath and the outer sheath, it is hard for the brush or the like to be inserted to the narrow space to be brought into direct contact with the filths and, hence, not only it takes a long time but also a need arises for the special cleaning device.

Further, probabilities occur with the occurrence of damage only to the outer sheath due to frequent use of the ultrasonic treatment device. In such cases, a need arises for the main unit to be replaced in its entirety. The reason comes from the fact that the operational main part, the inner sheath, the outer sheath and the operational force transfer member are formed in the substantially integrated fashion and it becomes hard to disassemble these component parts. Therefore, even if a need arises for replacing only the outer sheath of the main unit, an issue has arisen with an increase in cost for replacement.

SUMMARY OF THE INVENTION

The present invention has been made in consideration of the above drawbacks, and an object of the present invention is to facilitate cleaning in the inner space of an ultrasonic treatment device.

According to one aspect of the present invention, there is provided an ultrasonic treatment device comprising: a transducer unit equipped with an ultrasonic transducer generating ultrasonic vibration in response to supply of power; a probe unit configured to have a treatment member at a distal end thereof, detachably loaded to the transducer unit, and equipped with an ultrasonic probe transmitting the ultrasonic vibration to the distal end of the treatment member when the transducer unit is loaded to the probe unit; and a main unit which is manually grasped by an operator, to which the probe unit with the transducer unit loaded thereto is detachably loaded, and which has a cylindrical insert through which the ultrasonic probe is inserted to have the treatment member protruded outwardly when the probe unit is loaded and an outer sheath detachably covering an outer surface of the insert.

As a further aspect of the present invention, there is provided an ultrasonic treatment device comprising: a main unit having an operation member to be grasped and operated by an operator; an ultrasonic transducer; a treatment member; an ultrasonic probe being detachably loaded to the main unit and transmitting ultrasonic vibration generated by the ultrasonic transducer to the treatment member, the ultrasonic transducer being located at a base end of the probe and the treatment member being located at a distal and of the probe; an inner sheath approximately cylindrically shaped, arranged in the main unit, and configured to allow the ultrasonic probe to be inserted therethrough when the ultrasonic probe is loaded to the main unit; a jaw rotatably supported to face the treatment member of the ultrasonic probe at a distal end of the inner sheath when the ultrasonic probe is loaded to the main unit and formed to grip living tissue of the subject together with the treatment member, an operational force transfer member linking the jaw and the operation member, being able to move forward and backward on a surface of the inner sheath along an axial direction of the inner sheath, and transmitting to the jaw an operation force generated by the operation member; and an outer sheath detachably attached to the main unit to cover an outer surface of the inner sheath.

As anther aspect of the present invention, there is provided an ultrasonic treatment device comprising: a main unit grasped and operated by an operator; and a probe unit detachably loaded to the main unit and formed to transmit ultrasonic vibration from a base end of the probe unit to a distal end of the probe unit, the ultrasonic vibration being generated by an ultrasonic transducer and a treatment member being disposed at the distal end of the probe unit, wherein the main unit comprises an inner sheath through which the probe is inserted when the probe unit is loaded to the main unit, a jaw rotatably supported to face the treatment member at a distal end of the inner sheath and formed to grip living tissue of the subject together with the treatment member, an operation member disposed at a base end of the inner sheath and operated by the operator, an operational force transfer member linking the jaw and the operation member, being able to move forward and backward on a surface of the inner sheath along an axial direction of the inner sheath, and transmitting to the jaw an operation force generated by the operation member; and an outer sheath detachably attached to the main unit to cover an outer surface of the inner sheath.

Still, the present invention provides, as one aspect, a treatment apparatus comprising: a probe comprising an energy transmitting member and a treatment member and being used such that physical energy is transmitted to the treatment member through the energy transmitting member to allow the treatment member to medically treat living tissue of a subject to be treated; a device movably supported near to the treatment member by the probe and formed to be in charge of a cooperative operation for the living tissue together with the probe; an operation member used to provide an operation for moving the device from or to the treatment member; a first sheath which links the device and the operation member and through which the energy transmitting member is inserted; an operational force transfer member linking the device and the operation member, being movably disposed along an outer surface of the first sheath, and transmitting an operation force from the operation member to the device; and a second sheath detachably loaded to the operation member to cover the first sheath as well as the operation force transfer member.

BRIEF DESCRIPTION OF THE DRAWINGS

In the accompanying drawings:

FIG. 7A is a perspective view of the main unit of the ultrasonic treatment apparatus of the first embodiment; FIG. 7B is a schematic perspective view showing a part of the insertion member of the main unit; and FIG. 7C is a schematic perspective view showing a status wherein the part of the insertion member of the main unit, shown in FIG. 7B, is modified.

FIG. 8A is a plan view of the ultrasonic treatment apparatus of the first embodiment;

FIG. 8B is a schematic side view in partially cross-section showing a status as viewed in a direction as shown by an arrow 8B in FIG. 8A;

FIG. 8C is a cross-sectional view taken on line 8C-8C in FIG. 8B;

FIG. 8D is a cross-sectional view taken on line 8D-8D in FIG. 8B;

FIG. 10A is a schematic perspective view showing a status wherein the outer sheath is inserted from the distal end of the insertion member of the main unit of the ultrasonic treatment apparatus of the first embodiment or the outer sheath is removed from the insertion member of the main unit;

FIG. 10B is an exploded perspective view of the outer sheath of the ultrasonic treatment apparatus of the first embodiment;

DETAILED DESCRIPTION OF THE PREFERRED EMBODIMENTS

Hereinafter, various forms (hereinafter referred to as embodiments) for implementing this invention are described with reference to the accompanying drawings.

First Embodiment

Now, a first embodiment is described with reference to FIGS. 1 to 12.

Figure 1:
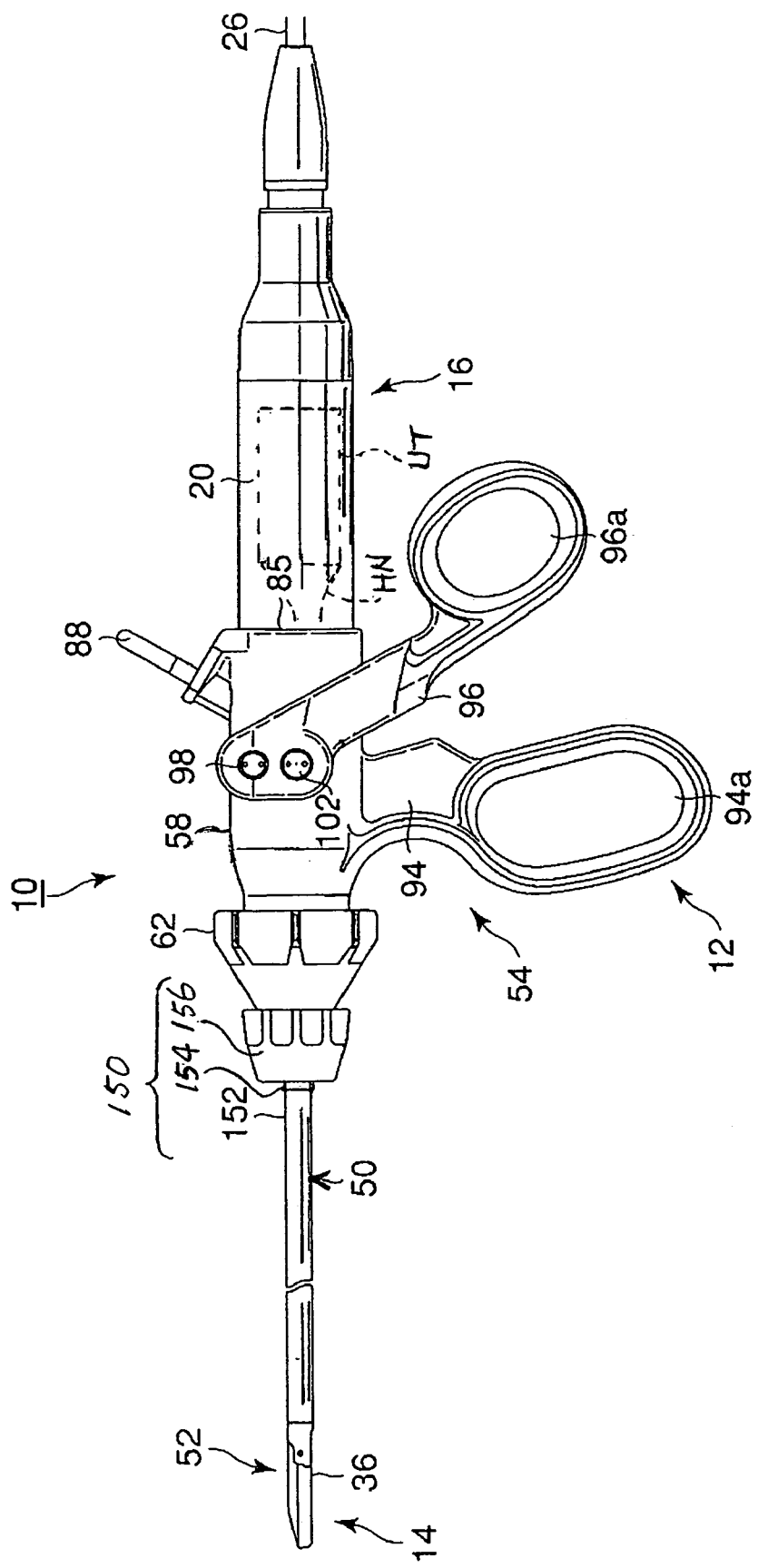
FIG. 1 is a schematic side view of an ultrasonic treatment apparatus of a first embodiment.

FIG. 1 shows an ultrasonic treatment device 10 of the first embodiment. The ultrasonic treatment device 10 and an apparatus main part AU form an ultrasonic treatment apparatus US.

Figure 2:
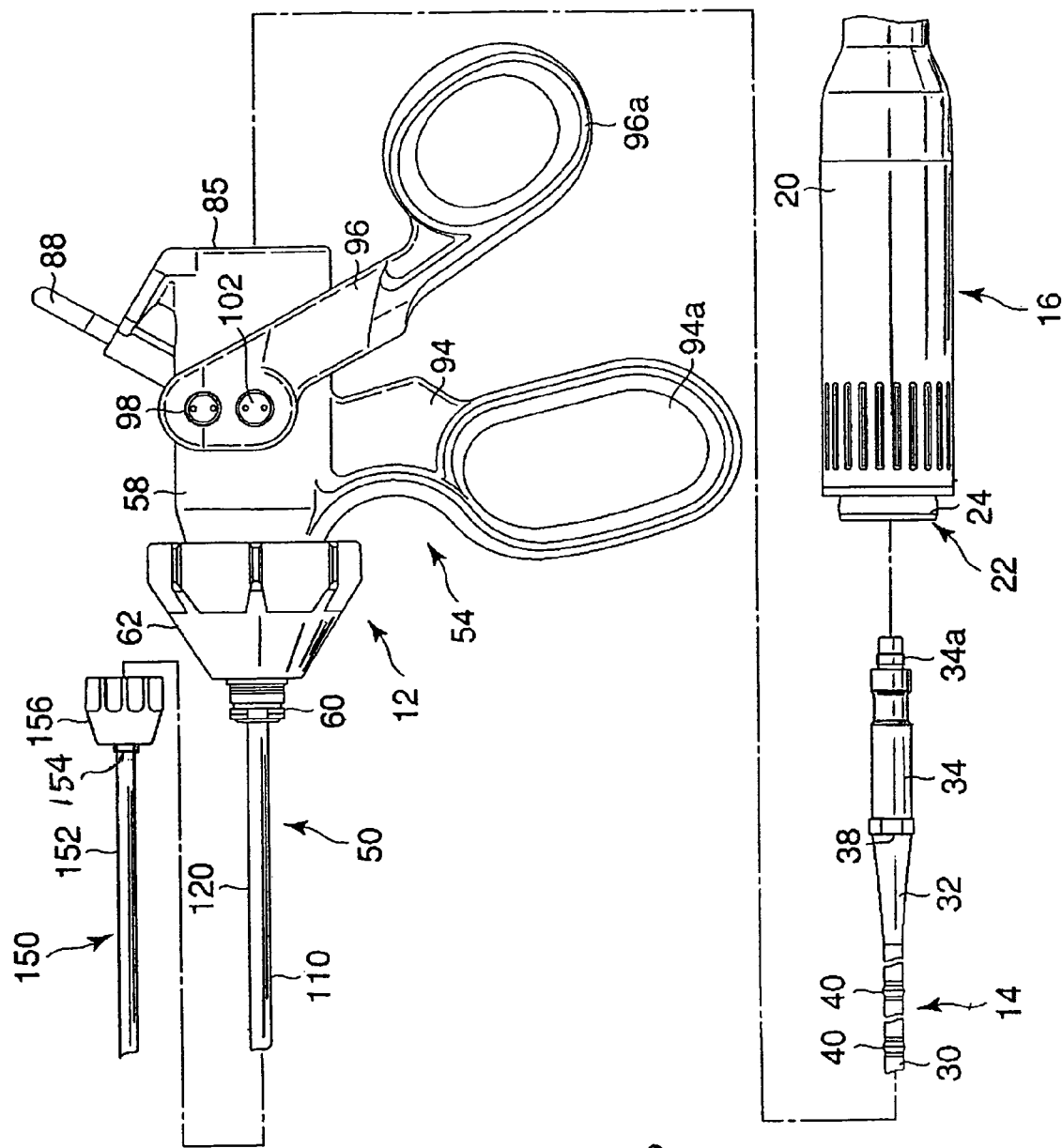
FIG. 2 is a schematic side view showing a status wherein the ultrasonic treatment apparatus of the first embodiment is exploded into a main unit, a probe unit, a transducer unit and an outer sheath.

The ultrasonic treatment device 10, shown in FIG. 1, is comprised of a main unit 12, a probe unit (ultrasonic probe) 14 and a transducer unit 16 as three main units, which are assembled to be detachable from each other. That is, the probe unit 14 is configured in the transducer unit 16 to be detachable therefrom (see FIG. 2). For this reason, a unit, in which the probe unit 14 and the transducer unit 16 are combined, can be detachably mounted to the main unit 12. That is, combining the main unit 12, the probe unit 14 and the transducer unit 16, as shown in FIG. 2, results in an assembly of the ultrasonic treatment device 10 as shown in FIG. 1.

Also, among the three principal units described above, the main unit 12 includes an outer sheath according to the present invention as a component part of the main unit 12. The outer sheath will be described later with reference to FIGS. 1, 2, 10A, 10B and 11.

Moreover, an entire configuration of the ultrasonic treatment device 10 under an assembled status is regarded to be substantially "bar shape" and a longitudinal direction of the bar shape is herein referred to as an "axial direction". Further, an area (at a left side in the drawing figure) closer to a distal end of the ultrasonic treatment device 10 in the axial direction is referred to as a "distal end", a "distal end side" or a "distal end portion" and, in addition, another area (at a right side in the drawing figure) closer to the apparatus main part AU of the ultrasonic treatment device 10 in the axial direction is referred to as a "base end", a "base end side" or a "base end portion".

The transducer unit 16 is comprised of a cylindrical transducer cover 20 and an ultrasonic transducer UT incorporated inside the cylindrical transducer cover 20 for producing ultrasonic vibration. The ultrasonic transducer UT has a distal end formed with a horn HN that amplifies amplitude of the generated vibration. A base end portion of the probe unit 14 is detachably mounted to a distal end of the horn HN.

As shown in FIG. 2, the transducer cover 20 has a distal end provided with a unit coupling member 22 through which the transducer cover 20 is detachably coupled to a transducer connecting member 85 (see FIG. 4) of an operational main part 58, which will be described below, of the main unit 12. Mounted onto an outer periphery of the unit coupling member 22 is a C-shaped engaging ring (C-ring) 24 that is partially cut out. As shown in FIG. 1, the transducer cover 20 has a rear end portion to which a power-supply connecting code, in which a transducer-use plug (not shown) is provided, is connected.

Figure 3:
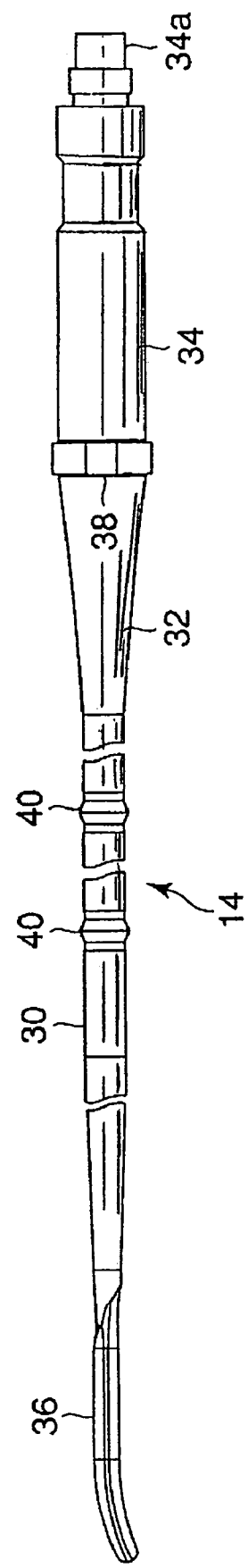
FIG. 3 is a schematic side view of the probe unit of the ultrasonic treatment apparatus of the first embodiment.

As shown in FIG. 3, the probe unit 14 is comprised of a vibration transmitting member (probe) 30, a horn part 32 formed on a base end portion of the vibration transmitting member 30, a maximum-diameter part 34 formed on a base end portion of the horn part 32, and a treatment member 36. A modified cross-section shape part 38, different in cross-section from a circular configuration, is provided between the horn part 32 and the maximum-diameter part 34. The modified cross-section shape part 38 has an outer peripheral surface formed with, for instance, parallel flat surfaces in opposition to each other. This enables the probe unit 14 to be mounted to a positioning member 80, which will be described later, of the main unit 12 in a predetermined position due to the flat parallel surfaces of the modified cross-section shape part 38.

The vibration transmitting member 30 has an outer peripheral surface on which a plurality of flange-shaped support members 40 are disposed at nodes of a standing wave of ultrasonic vibration to be transferred from a base end side of the vibration transmitting member 30 toward a distal end thereof. These support members 40 are formed of resilient material such as, for instance, rubber or the like, in ring shapes, respectively.

The maximum-diameter part 34 has a base end portion provided with a mounting screw 34a that is coupled to a probe mounting member (not shown) of the distal end of the horn HN of the transducer unit 16. The mounting screw 34a is screwed into a threaded bore part of the probe mounting member of the transducer unit 16. Therefore, the probe unit 14 and the transducer unit 16 can be unitarily assembled. The horn part 32 between the maximum-diameter part 34 and the vibration transmitting member 30 serves to amplify the amplitude of the ultrasonic vibration transferred from the transducer unit 16. The vibration transmitting member 30 transmits the ultrasonic vibration, whose amplitude is amplified with the horn part 32, toward the distal-end treatment member 36. The distal-end treatment member 36 is provided for the purpose of executing surgical treatment (hereinafter, merely referred to as "treatment") in contact with a living tissue through the use of energy resulting from the ultrasonic vibration. The distal-end treatment member 36 is formed in an asymmetric shape, that is, a circular-arc configuration curved in a direction deviated from a central axis aligned on an axial direction of the vibration transmitting member 30.

As shown in FIG. 1, the main unit 12 is comprised of an elongated tubular insertion member 50, a distal-end operating portion 52 formed at a distal end of the insertion member 50, and an operating portion 54 disposed at a base end portion of the insertion member 50.

Figure 4:
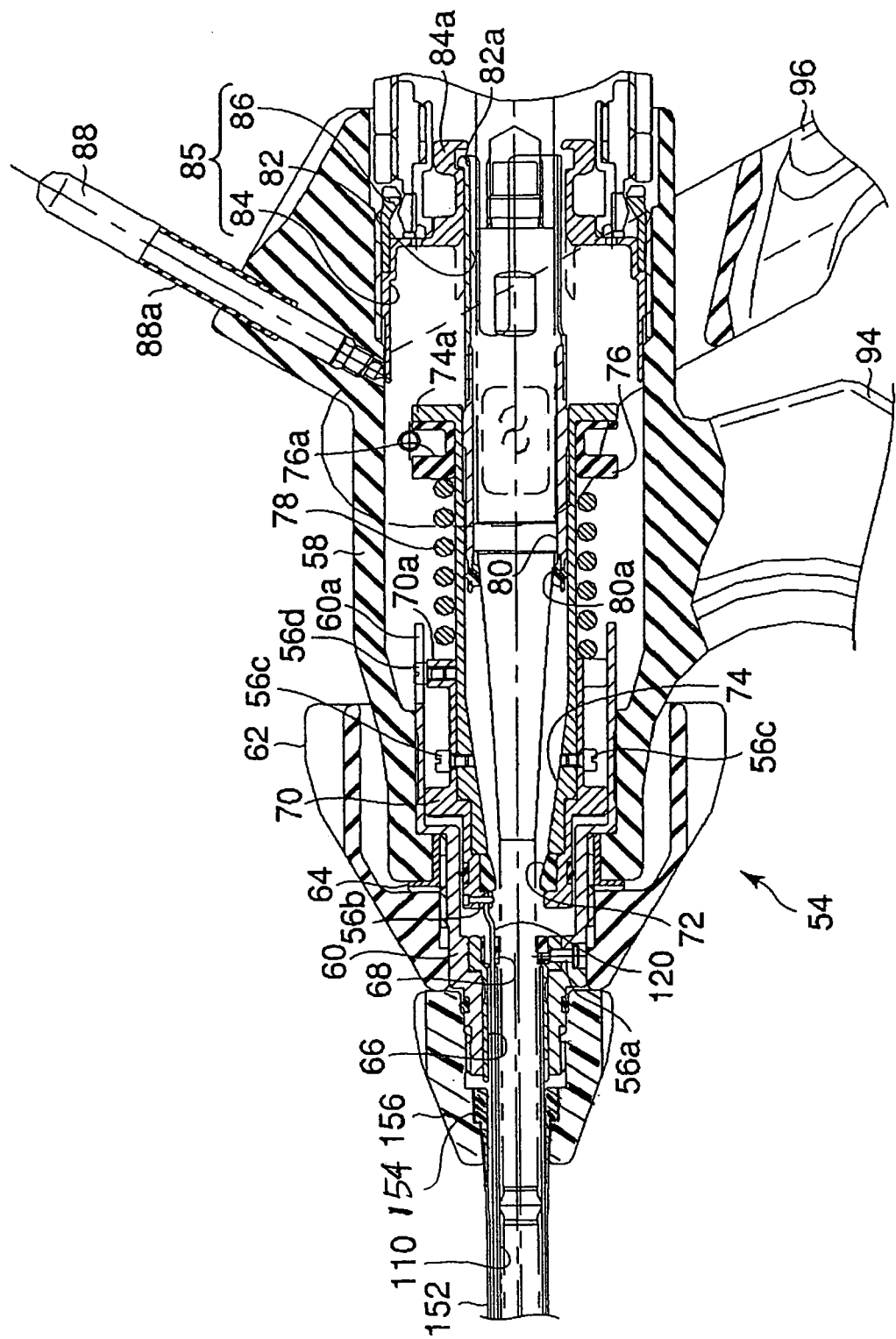
FIG. 4 is a schematic side view of a neighborhood of an operating portion of the ultrasonic treatment apparatus of the first embodiment.
Figure 5:
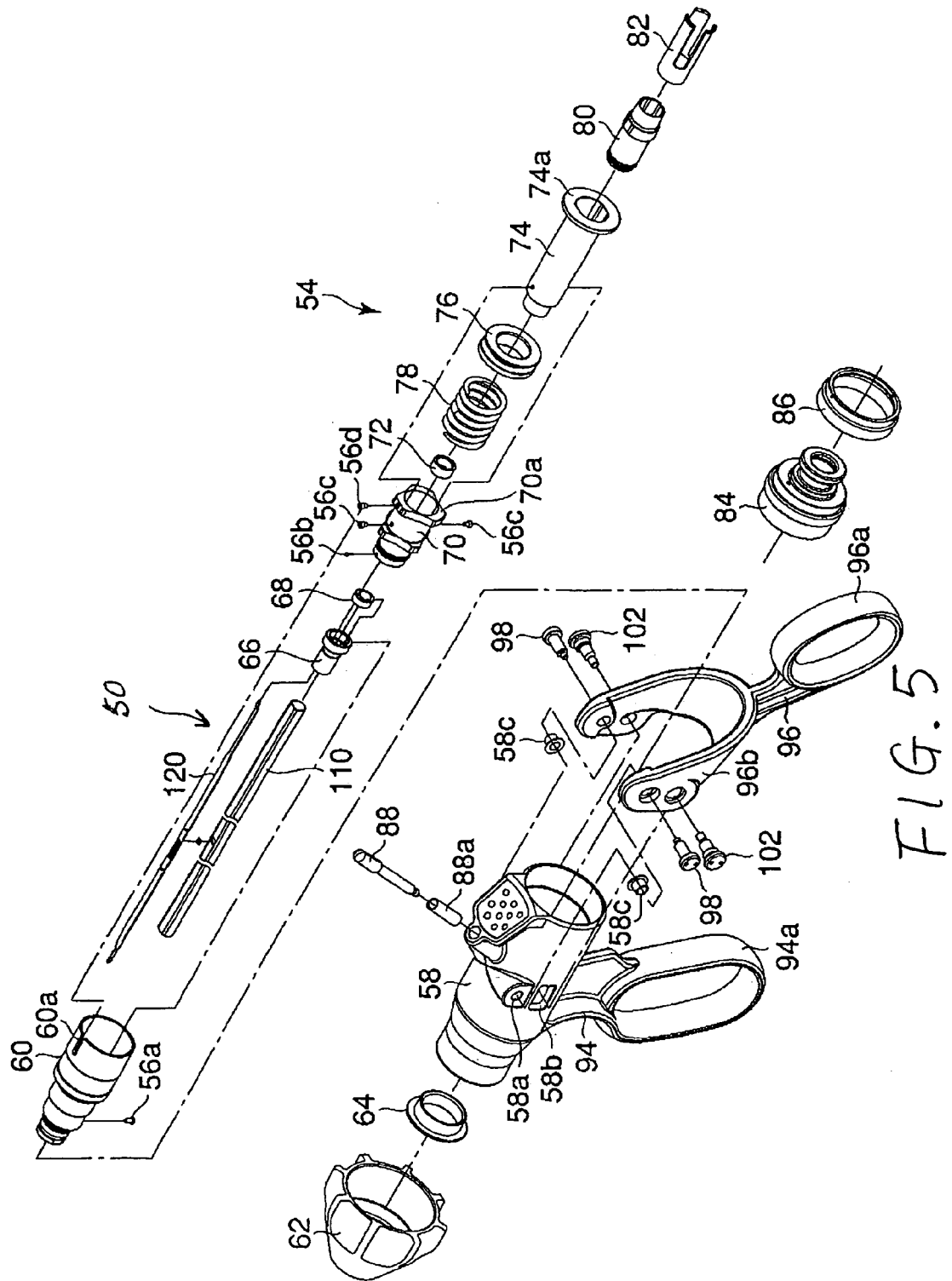
FIG. 5 is a schematic exploded perspective view of the main unit of the ultrasonic treatment apparatus of the first embodiment.

As shown in FIGS. 4 and 5, the operating portion 54 includes an operational main part 58, having insulation property, which is formed in a hollow portion. The operational main part 58 has a distal end provided with a cylindrical rotation-link member 60 with electrical conductivity. The rotation-link member 60 has a small-diameter part, a medium-diameter part and a large-diameter part formed in such an order from a distal end of the rotation-link member 60 toward a base end thereof. The medium-diameter part has an intermediate diameter between the small-diameter part and the large-diameter part and has an outer periphery formed with a male threaded portion. The large-diameter part has a base end portion formed with a slit 60a extending in the axial direction. Steps are formed between the small-diameter part and the medium-diameter part and between the medium-diameter part and the large-diameter part, respectively.

A rotary knob 62, having electrical insulation, is screwed onto an outer peripheral surface of the medium-diameter part of the rotation-link member 60. A fixture ring 64 is screwed onto a base end side of the rotary knob 62 at the outer periphery of the medium-diameter part. The operational main part 58 is sandwiched between a flange portion of the fixture ring 64 and the rotation-link member 60. The fixture ring 64 is slidable along the medium-diameter part with respect to the operational main part 58 such that rotating the rotary knob 62 allows the rotation-link member 60 to be rotated.

A tabular sheath connecting member 66 with electric conductivity, to which a base end portion of an inner sheath, described below, is fixedly secured, and a ring-shaped operational rod guide member 68, disposed an inner peripheral surface of a base end portion of the sheath connecting member 66 to guide a base end portion of an operational rod (operational force transfer member) 120, described below, are fixedly secured to an inner peripheral wall of the distal end of the rotation-link member 60 by means of a first pin 56a. The operational rod guide member 68 has a through-bore through which the operational rod 120, described below, penetrates in parallel to a central axis of the operational rod guide member 68. Thus, the operational rod 120 is placed in and guided by the through-bore to be movable forward or rearward. The operational rod guide member 68 is made of resin material such as, for instance, PTFE (polytetrafluoroethylene) or the like and prevents the vibration transmitting member 30 from being brought into contact with a metallic member such as the operational rod 120.

A tabular operational rod connecting member 70 with electrical conductivity and a protector ring 72, disposed inside an inner peripheral surface of the operational rod connecting member 70, are disposed on the inner peripheral side of the rotation-link member 60 at a side closer to base ends of the sheath connecting member 66 and the operational rod guide member 68. The operational rod 120 has the base end that is fixedly secured to the operational rod connecting member 70 by means of a second pin 56b. The protector ring 72 is made of resin material such as, for instance, PTFE and prevents the vibration transmitting member 30 from being brought into contact with a metallic member such as the operational rod connecting member 70.

A tubular slider receiving member 74 with electrical conductivity is disposed in an inner periphery of the operational rod connecting member 70 at a side closer to a base end portion of the protector ring 72. The operational rod connecting member 70 and the slider receiving member 74 are fixedly secured to each other through a pair of opposing third pins 56c.

The operational rod connecting member 70 has a base end formed with a radially and outwardly extending flange portion 70a. A fourth pin 56d, received in the slit 60a of the rotation-link member 60, is tightened onto the flange portion 70a of the operational rod connecting member 70. Thus, the fourth pin 56d is moveable along the slit 60a of the rotation-link member 60. Further, as the rotary knob 62 is rotated, the rotation-link member 60 also rotates and the operational rod connecting member 70 also rotates. That is, as the rotary knob 62 is rotated, the rotation-link member 60, the operational rod connecting member 70, the slider receiving member 74 and the operational rod 120 rotate.

The slider receiving member 74 has a base end formed with a radially outwardly protruding flange portion 74a. A substantially ring-shaped slider 76 with insulation property is carried on an outer peripheral surface of the slider receiving member 74 between the flange portion 70a of the operational rod connecting member 70 and the flange portion 74a of the slider receiving member 74. A drive force limit spring 78 is disposed on the outer peripheral surface of the slider receiving member 74 between the flange portion 70a of the operational rod connecting member 70 and the slider 76. The slider 76 has an outer periphery formed with a recess-like pin receiving part 76a that receives acting pins 102 of a movable handle 96 that will be described below.

Therefore, when performing closing movement of the movable handle 96, described below, relative to a stationary handle 94, the slider 76 is pressed toward the distal end of the operational main part 58 due to the acting pins 102. In contrast, when performing opening operation, the slider 76 is pressed rearward of the operational main part 58. The slider 76 is urged toward the flange portion 74a of the slider receiving member 74 by the action of the drive force limit spring 78. Under circumstances where the magnitude of a force exerted to the drive force limit spring 78 is less than the magnitude of an equipped force when the movable handle 96 is closed, the slider 76, the drive force limit spring 78, the slider receiving member 74 and the operational rod connecting member 70 are simultaneously moved in a distal-end direction along the inner peripheral surface of the rotation-link member 60 and the outer peripheral surface of the positioning member 80 described above. Also, this results in movement of the operational rod 120.

In the meanwhile, when an attempt is made to close the movable handle 96 to a further extent with the forward movement of the operational rod 120 being restricted such as when the living tissue is grasped, the drive force limit spring 78 is compressed at a timing when the magnitude of the force exerted to the drive force limit spring 78 exceeds the magnitude of the equipped force. This causes only the slider 76 to move in the distal-end direction along the outer peripheral surface of the slider receiving member 74, thereby preventing the operational rod 120 from being applied with a force greater than a fixed value.

A tubular positioning member 80, to which an outer peripheral surface of the modified cross-section shape part 38 (see FIG. 3) is mounted for positioning capability, is fitted to and secured to the inner peripheral surface of the base end of the slider receiving member 74. To this end, an inner peripheral surface of the positioning member 80 is formed in a shape to allow the modified cross-section shape part 38 of the probe unit 14 to be mounted. The positioning member 80 has a base end to which a distal end of a contact pipe 82 with electrical conductivity is connected upon fitting engagement. The contact pipe 82 has a base end formed with radially and outwardly extending protrusions 82a.

A transducer unit guide 84 with electrical conductivity is disposed on an outer periphery of the contact pipe 82. This guide 84 has a base end whose inner peripheral surface is formed with a protrusion receiving part 84a that receives the protrusions 82a of the contact pipe 82. Therefore, the contact pipe 82 and the guide 84 are held in engagement for rotating capabilities with respect to each other due to the engagement between the protrusions 82a and the protrusion receiving part 84a. A C-ring receiving member 86 is disposed on an outer peripheral surface of a distal end of the guide 84 to receive an engagement ring (C-ring) 24 shown in FIG. 2. Thus, the C-ring receiving member 86 and the guide 84 form a transducer connecting member 85 with which the unit coupling member 22 of the transducer unit 16 engages.

A high-frequency connector pin 88, covered with an insulative cover 88a and available to be electrically connected to a high-frequency power supply (power supply for an electric cautery device), is mounted to an upper area of the operational main part 58 at the base end thereof at an angle inclined rearward. The high-frequency connector pin 88 is held in abutting engagement with an outer peripheral surface of the transducer unit guide 84. The inner peripheral surface of the guide 84 is connected to the contact pipe 82 and, so, to the positioning member 80. The positioning member 80 has a distal end that has an inner peripheral surface on which a rubber ring (electric connecting part) 80a with electrical conductivity is provided. Thus, the high-frequency connector pin 88 and the rubber ring 80a are electrically connected to each other. The rubber ring 80a is held in abutting engagement with the outer peripheral surface of the probe unit 14 under a status where the probe unit 14 is set to the positioning member 80.

Therefore, as a high frequency current is conducted from the high-frequency connector pin 88, this high frequency current is delivered to the probe unit 14. Also, when this takes place, under a status wherein ultrasonic vibration is transferred to the probe unit 14, the rubber ring 80a is located in a position near the node of vibration.

As shown in FIG. 5, the stationary handle 94 and the movable handle 96, rotatable with respect to the stationary handle 94, are provided on the operational main part 58 at the outer peripheral thereof in integrated relationship with the operational main part 58. An operational end portion of the stationary handle 94 is formed with a finger hole 94a on which a finger other than the thumb is selectively placed. An operational end portion of the movable handle 96 is formed with a finger hole 96a on which the thumb of the same hand is placed.

The outer peripheral surface of the operational main part 58 is formed with a pair of pivot-pin receiving parts 58a and a pair of acting-pin operation windows 58b. The acting-pin operation windows 58b penetrate through a wall portion of the operational main part 58. Bifurcated connecting parts 96b are formed on upper end portions of the movable hand 96. Pivot pins 98 are mounted to the upper end portions of the movable hand 96 via collars (insulation caps) 58c fitted to the pivot-pin receiving parts 58a, respectively. The collars 58c are made of members with low coefficient of friction to allow the movable handle 96 to smoothly rotate. These pivot pins 98 are coupled to the operational main part 58 in an area, shown in FIG. 4, above an axis line on which the outer sheath 150, described below, is mounted to the main unit 12. Thus, the movable handle 96 is movable in opening and closing capabilities with respect to the stationary handle 94.

At the upper end of the movable handle 96, the acting pins 102 extend through the acting-pin operation windows 58b, respectively, to be disposed in the pin receiving part 76a of the slider 76. Therefore, as the movable handle 96 is opened or closed about a pivotal point of the pivot pins 98 with respect to the stationary handle 94, the acting pins 94 cause the slider 76 to move forward or rearward.

Figure 6:
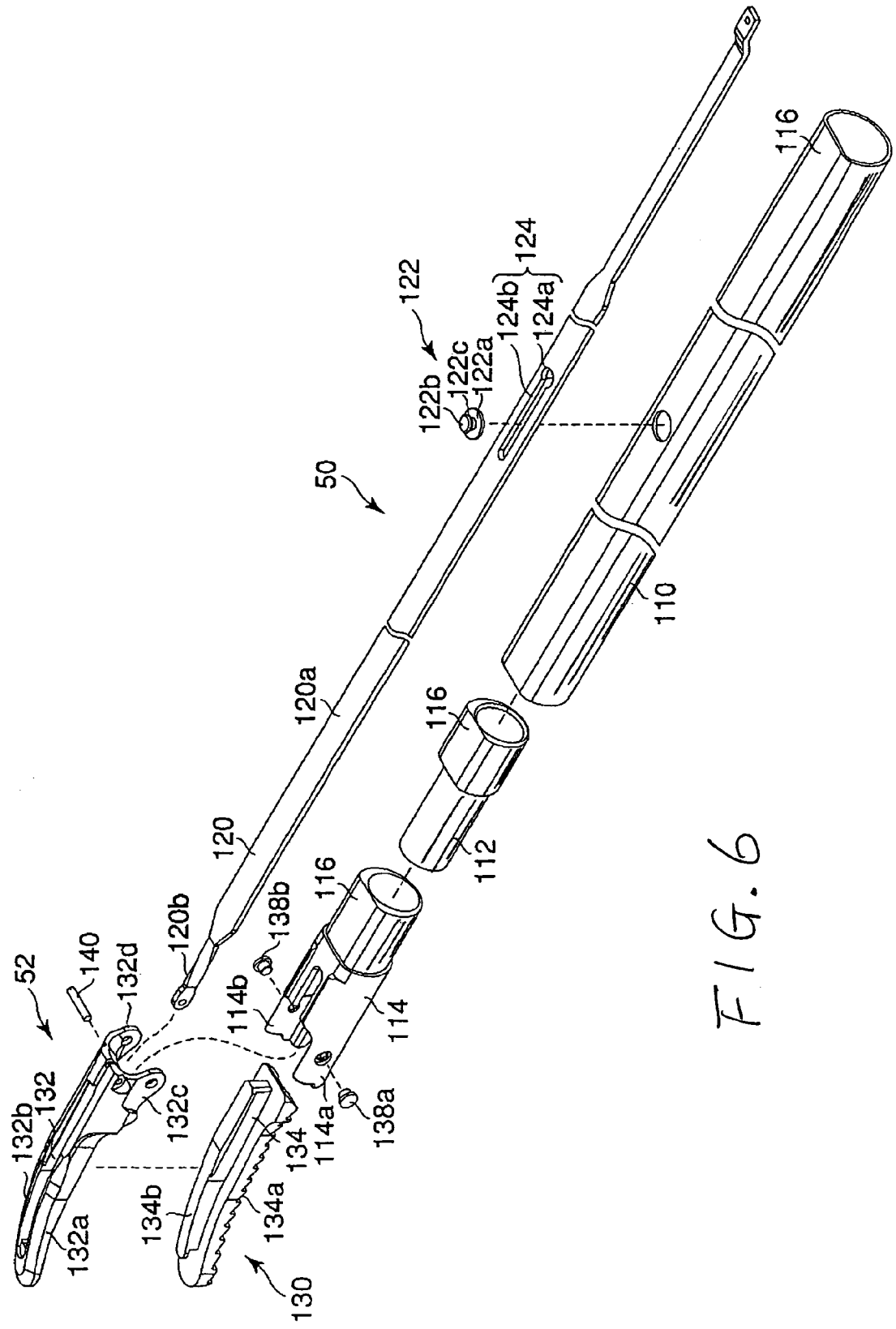
FIG. 6 is a schematic exploded perspective view of an insertion member and a distal-end operating portion of the main unit of the ultrasonic treatment apparatus of the first embodiment.

FIG. 6 shows the insertion member 50 that plays a role as a component element of the distal end of the main unit 12. The insertion member 12 is comprised of an inner sheath 110 (first sheath), a tubular connecting member 112 provided on a distal end of the inner sheath 110, and a jaw holding member 114 provided on a distal end of the connecting member 112. The inner sheath 110, the connecting member 112 and the jaw holding member 114 are formed in a substantially D-shape in cross-section with all of these component parts being formed with flat surface portions 116, respectively.

Thus, the connecting member 112 and the jaw holding member 114 have base end portions are fitted to and fixedly secured to a distal end of the inner sheath 110 under conditions where the connecting member 112 and the jaw holding member 114 are positioned in a predetermined orientation. The base end portion of the jaw holding member 114 is fitted to a distal end portion of the connecting member 112. The operational rod 120 is placed on the flat surface portion 116, formed on the inner sheath 110 at the outer peripheral surface, to be movable forward or rearward along the axial direction of the insertion member 50.

A limit pin 122 is mounted to the flat surface portion 116 at a substantially intermediate position between the distal end and the base end of the inner sheath 110. The inner pin 122 includes discs 122a, 122b that have discoid shapes, respectively, and are mutually parallel to each other, and a short rod portion 122c by which the discs 122a, 122b are connected. The first disc 122a has a large diameter than that of the second disc 122b. The first disc 122a is secured to the flat surface portion 116 of the inner sheath 110 by suitable means such as welding. It is preferable that a plurality of such limit pins 122 are provided on the flat surface portion 116 of the inner sheath 110.

The operational rod 120 takes the form of a rod main part 120a made of a thin plate-like member that is substantially flat in shape and flexible. The operational rod 120 has a distal end portion formed with a jaw coupling part 120b that is twisted at an angle of approximately 90° with respect to the laterally oriented rod main part 120a and bent in a vertical direction. The jaw connecting part 120b and upper edge sides of respective leg portions 132c, 132d of a jaw main part 132, described below, are rotatably coupled to each other by means of the connecting pin 140.

The operational rod 120 is formed with a slit 124 in a given length along an axial direction of the rod main part 120a at a substantially intermediate position between the distal end and the base end of the operational rod 120. The slit 124 includes a circular aperture 124a, larger in diameter than the second disc 122b of the limit pin 122, which is formed in a position closer to the base end of the rod main part 120a, and an oblong aperture 124b formed to be integral with the circular aperture 124a in a substantially elongated shape at a position closer to the distal end of the rod main part 120a.

Penetrating the second disc 122b through the circular aperture 124a allows the rod portion 122c of the limit pin 122 to move relative to the oblong aperture 124b of the operational rod 120 as shown in FIGS. 7A and 7B and FIGS. 8A to 8C. Such slits 124 may be preferably formed in the rod main part 120a at a plurality of areas thereof. Thus, even if the operational rod 120 is moved forward or rearward within a given range, the presence of the slit 124 precludes the operational rod 120 from escaping from the flat surface portion 116 or the operational rod 120 from flexing. In such a way, the slit 124 of the operational rod 120 and the limit pin 122 of the flat surface portion 116 constitute a forward and rearward movement limiting mechanism that precludes a forward and rearward movement direction of the operational rod 120 to be deviated from the axial direction of the inner sheath 110.

Further, the distal-end operating portion 52 of the main unit 12 is described with reference to FIG. 6. As shown in FIG. 6, the distal-end operating portion 52 is comprised of the jaw holding member 114, and a single swinging type jaw unit 130 rotatably mounted on a distal end of the jaw holding member 114 for grasping the living tissue.

The jaw unit 130 includes a jaw main part 132 with its base end formed in a substantially arch-shaped configuration, and a grasping member 134 for grasping an object (living tissue).

The jaw main part 132 has a pair of arms 132a, 132b with distal ends thereof being connected to each other while their base ends are diverged into bifurcated configurations. Thus, the base end of the jaw main part 132 is formed with a given space.

The grasping member 134 is formed of material with low-frictional resistance such as, for instance, PTFE or the like that has heat resistance while providing lowered frictional resistance to an associated component member in contact with the grasping member 134. The grasping member 134 has a contact surface, to be held in contact with the living tissue of an object to be incised and coagulated, which is formed with a plurality of nonslip teeth in juxtaposed positions, resulting in the formation of nonslip teeth 134a in a saw-tooth appearance. The nonslip teeth 134a makes it possible to grasp the living tissue of the object to be incised and coagulated. A protruding portion 134b, available to be disposed in fitting engagement between the pair of arms 132a, 132b of the jaw main part 132, is formed on the grasping member 134 at a side opposite to the other surface thereof to be brought into contact with the living tissue. Therefore, the grasping member 134 is fitted to and mounted in a gap of the jaw main part 132 as shown in FIGS. 9B and 9C.

The respective arms 132a, 132b of the jaw main part 132 have base ends formed with leg portions 132c, 132d that are coupled to arms 114a, 114b formed at the distal end of the jaw holding member 114 via pivot pins 138a, 138b, respectively. Thus, the arms 114a, 114b at the distal end of the jaw holding member 114 and the leg portions 132c, 132d at the base end of the arms 132a, 132b of the jaw main part 132 are coupled to each other via the pivot pins 138a, 138b, respectively. That is, the jaw unit 130 is rotatable with respect to the distal end of the jaw grasping member 114.

A pin-bored insertion part is formed in the jaw main part 132 on a position above upper edges of the leg portions 132c, 132d at the base ends of the respective arms 132a, 132b to allow the jaw coupling part 120b of the distal end of the operational rod 120 and the coupling pin 140 to be coupled to each other. Thus, the jaw coupling part 120b, formed at the distal end of the operational rod 120, and the respective arms 132a, 132b of the jaw main part 132 are coupled to each other by means of the coupling pin 140. That is, as the operational rod 120 is moved forward or rearward along the flat surface portion 116, the jaw unit 130 is rotated relative to the distal end of the jaw holding member 114.

Now, as the operational rod 120 is moved forward toward a distal end side thereof, the jaw unit 130 is closed. During closing operation of the jaw unit 130, pressing the grasping member 134 of the jaw unit 130 against the treatment member 36 of the vibration transmitting member 30 allows the object (living tissue) to be grasped between the treatment member 36 and the grasping member 134 of the jaw unit 130. Also, the jaw unit 130 is also used for peeling off the living tissue.

Figure 9A:
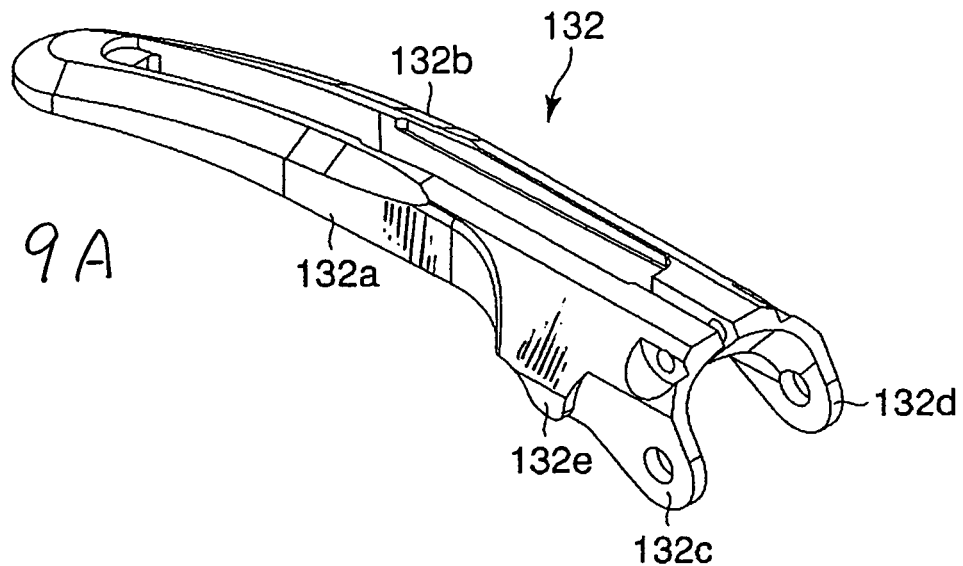
FIG. 9A is a schematic perspective view showing a jaw main part of a jaw unit of a distal-end operating portion of the main unit of the ultrasonic treatment apparatus of the first embodiment.
Figure 9B:
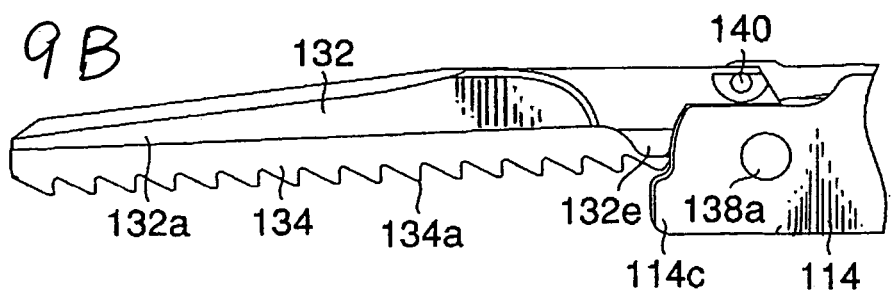
FIG. 9B is a schematic side view showing a status wherein a projecting portion of the jaw main part of the jaw unit of the ultrasonic treatment apparatus of the first embodiment.
Figure 9C:
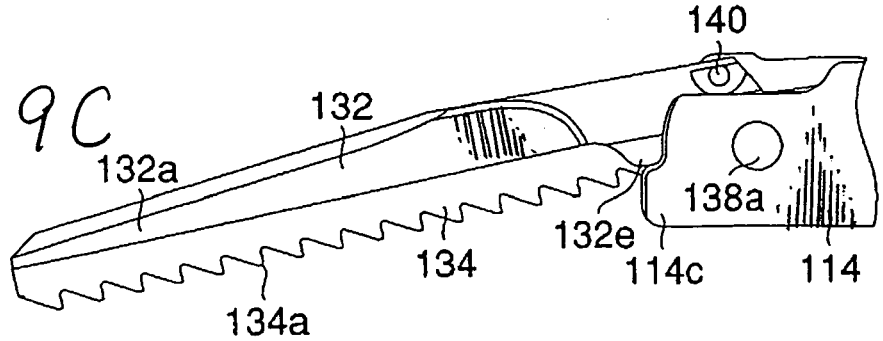
FIG. 9C is a schematic side view showing a status wherein the projecting portion of the jaw main part of the jaw unit of the ultrasonic treatment apparatus of the first embodiment is brought into abutment with a protrusion of a jaw holding member.

By the way, as shown in FIG. 9A, the base ends of the arms 132a, 132b of the jaw main part 132 have the base end surfaces formed in the arch-shapes, respectively, as set forth above. For this reason, when comparing the strengths of the base ends of the arms 132a, 132b and the strengths of the leg portions 132c, 132d to the strengths of these component parts formed in increased wall thickness, the base ends of the arms 132a, 132b and the strengths of the leg portions 132c, 132d have strengths greater than those of structures wherein they are formed in substantially rectangular shapes or U-shapes. That way, the base ends of the arms 132a, 132b and the leg portions 132c, 132d are formed in walls with less thickness than those of the case taking the substantially rectangular shapes or U-shapes while maintaining similar strengths. Accordingly, the base end of the jaw main part 132 is made smaller in size than that of the structures formed in the substantially rectangular shapes or U-shapes.

Projecting portions 132e are formed on outer peripheries of the arms 132a, 132b of the jaw main part 132 at positions forward of the leg portions 132c, 132d, respectively. The projecting portions 132e are formed to be greater in wall thickness than those of the leg portions 132c, 132d.

As shown in FIGS. 9B and 9C, protrusions 114c are formed on the arms 114a, 114b at the distal end of the jaw holding member 114 for abutting engagement with the projecting portions 132e of the jaw main part 132, respectively. If attempt is made to minimize a diameter of the jaw holding member 114 to be as small as possible, thin-wall portions 114c, 114d are formed as shown in FIG. 8D. Therefore, as a strong external force acts in a direction to close the distal-end operating portion 52 under a condition where no probe unit 14 is mounted, stresses are caused to concentrate on the thin-wall portions 114c, 114d resulting in a probability with the occurrence in damage to the jaw holding member 114. However, by taking the structure described in conjunction with the embodiment, since the projecting portions 132e, each with increased wall thickness, and the protrusions 114c of the jaw holding member 114 are initially brought into abutment with each other as shown in FIG. 9C, no further forces are exerted to the thin-wall portions 114c, 114d. Further, upon arbitrarily altering such an abutment angle such that the distal-end operating member 52 is further hard to be closed, even with the probe unit 14 mounted to the distal-end operating member 52, the projecting portions 132e of the jaw main part 132 are caused to abut against the protrusions 114c of the jaw holding member 114 after the probe unit 14 is flexed to some extent when the distal-end operating member 52 is closed with a force exceeding a certain magnitude of force. Thus, no further force is exerted to the distal-end operating member 52 in a closing direction and, hence, it becomes possible to prevent excessive force from being applied to the probe unit 14.

Figure 11:
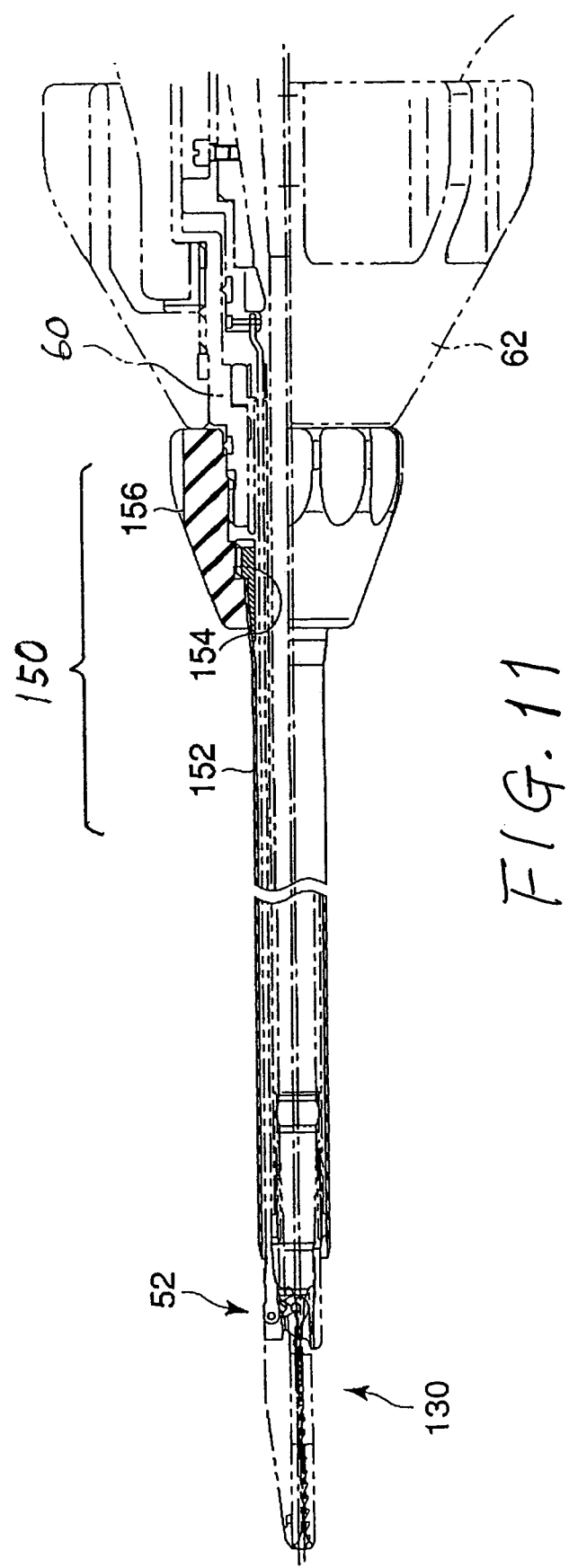
FIG. 11 is a schematic cross-sectional view, partially cutaway, showing a status wherein the outer sheath is inserted from the distal end of the insertion member of the main unit of the ultrasonic treatment apparatus of the first embodiment.
Figure 12:
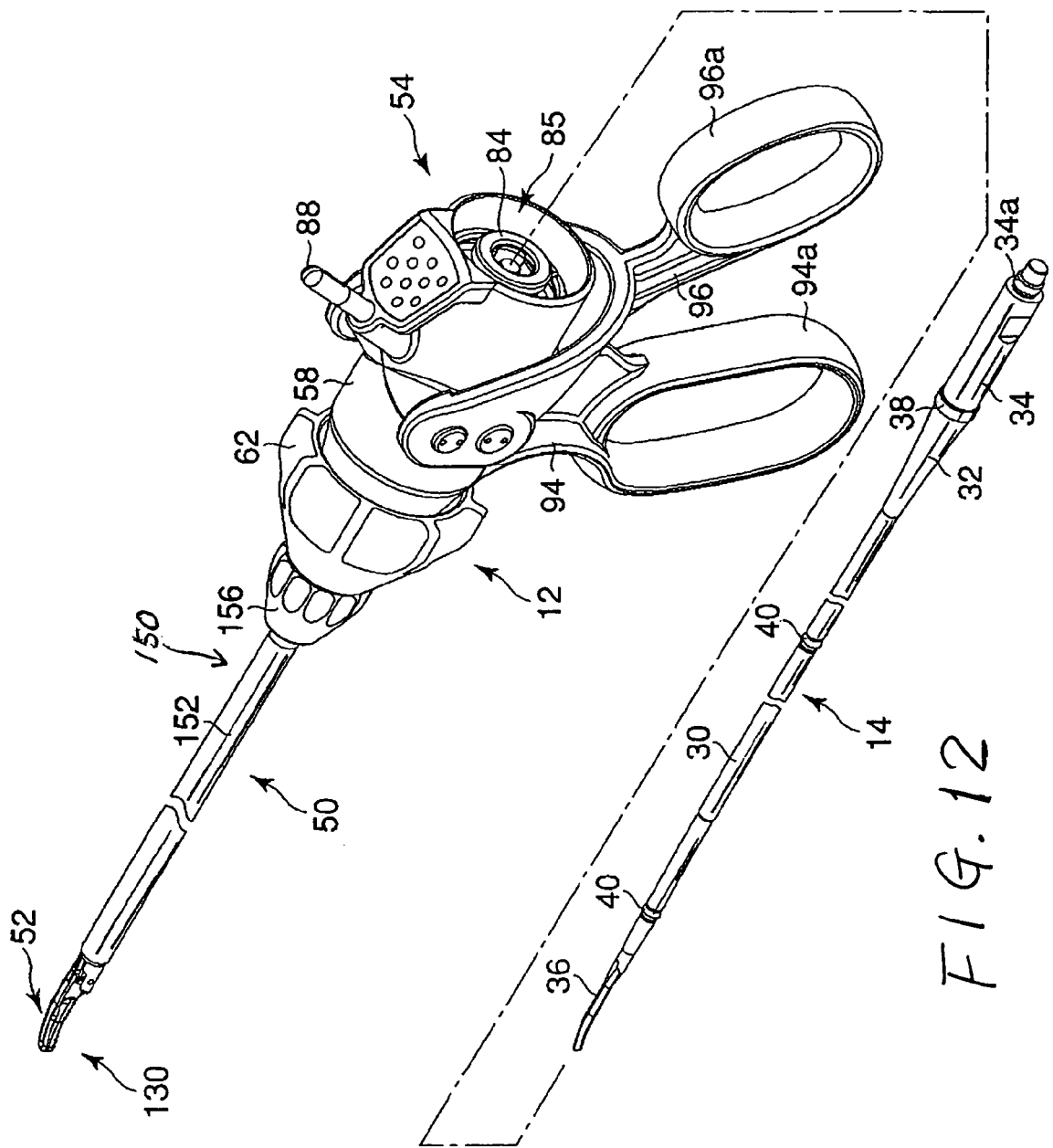
FIG. 12 is a schematic perspective view showing a status wherein the probe unit is inserted from a base end of the operating portion of the main unit of the ultrasonic treatment apparatus of the first embodiment or the probe unit is removed from the operating portion of the main unit.

Further, the outer sheath (second sheath), forming a part of the main unit 12, is described with attention focused on FIGS. 10A, 10B and 11. This outer sheath forms a principal part of features of the present invention.

As shown in FIG. 10A, the outer sheath 150 is detachably mounted to outer peripheral walls of the inner sheath 110 of the insertion member 50, the coupling member 112 and the jaw holding member 114.

As shown in FIG. 10B, the outer sheath 150 is comprised of a sheath case main part 152, a connecting member 154 disposed on a base end of the sheath case main part 152, and a connector 156 disposed on an outer periphery of the connecting member 154.

As shown in FIG. 11, the connector 156 has a threaded inner peripheral surface that can be screwed onto an outer peripheral surface of a small diameter portion of a distal end of the rotation-link member 60. Also, although not shown, the connector 156 may be preferably configured in structure with a click mechanism through which the connector 156 can be engageable with the outer peripheral surface of the small diameter portion at the distal end of the rotation-link member 60.

Now, operations of the ultrasonic treatment device 10 of the presently filed embodiment are described.

The ultrasonic treatment device 10 is described in conjunction with a structure wherein the main unit 12, the probe unit 14 and the transducer unit 16 are separate from each other as shown in FIG. 2. Additionally, the outer sheath 150 is separated from the main unit 12.

In assembling the ultrasonic treatment device 10, the outer case 150 is covered on the insertion member 50 in a way to allow the distal-end operating member 52 of the insertion member 50 of the main unit 12 to be put into the outer sheath 150 (that is, the connector 156, the connecting member 154 and the heath main part 152). This covering step may be simply completed by merely screwing the connector 156 onto the outer peripheral surface of the small diameter portion at the distal end of the rotation-link member 60 at the distal end of the operational main part 58.

Further, the probe unit 14 and the transducer unit 16 are coupled to each other as shown in FIG. 2. In this case, a mounting thread 34a formed at the distal end of the probe unit 14 is screwed into a threaded bore portion formed in a probe mount part at the distal end of the horn of the transducer unit 16.

The probe unit 14, under such a status, is inserted from the base end of the main unit 12 toward the distal end of the insertion member 50. The unit coupling member 22 (see FIG. 2) of the transducer unit 16 is mounted to the base end of the main unit 12. Then, the unit coupling member 22 of the transducer unit 16 is brought into engagement with the transducer connecting member 85 having the transducer unit guide 84 (see FIG. 4) of the main unit 12 and the C-ring receiving member 86.

The modified cross-section shape part 38 (see FIG. 2) of the probe unit 14 is positioned in a location determined by the positioning member 80 of the main unit 12. Therefore, the treatment member 36 of the probe unit 14 stands face to face with the distal-end operating member 52 of the main unit 12 in a direction determined by an operator.

Accordingly, the transducer connecting member 85 at the distal end of the main unit 12 is brought into engagement with the unit coupling member 22 at the distal end of the transducer unit 16 into an assembly of the ultrasonic treatment device 10 (see FIG. 1).

As electric current is caused to flow through the ultrasonic transducer of the transducer unit 16 via the power supply connecting chord 26, the ultrasonic transducer begins to vibrate. This ultrasonic vibration is transmitted from the base end of the probe unit 14 toward the treatment member 36 at the distal end of the probe unit 14. Under such a status, as the movable handle 96 is operated to come close (to be closed) to the stationary handle 94 about the axis of the pivot pin 98, the slider 76 is moved toward the distal end of the insertion member 50 via the acting pins 102. When this takes place, due to the urging force of the drive force limit spring 78, the operational rod connecting member 70 is moved toward the distal end of the insertion member 50. Therefore, the operational rod 120 is moved toward the distal end of the insertion member 50. In this moment, the operational rod 120 is sustained under a sliding condition along the flat surface portion 116.

The jaw main part 132 is pushed outward in the forward area by means of the coupling pin 140 at the distal end of the operational rod 120. For this reason, the jaw main part 132 is rotated about the pivot axes of the pivot pins 138*a*, 138*b*. That is, the grasping member 134, fitted to the jaw main part 132, is caused to come close to the treatment member 36 of the probe unit 14. Therefore, the living tissue is gripped between the treatment member 36 of the probe unit 14 and the grasping member 134 of the jaw unit 130, thereby performing ultrasonic treatment.

A high frequency cable is connected to the high-frequency connector pin 88 mounted on the operational main part 58. Under such a status, high frequency current is supplied from the high frequency power supply to the high frequency cable. Then, the high frequency current is applied to the horn part 32 of the probe unit 14 from the conductive rubber ring 80*a* via the high-frequency connector pin 88, the transducer unit guide 84, the contact pipe 82 and the positioning member 80. Thus, the high frequency current is delivered to the treatment member 36 of the probe unit 14 to cause the discharge ends of the treatment member 36 to discharge electricity for performing high frequency treatment.

After the ultrasonic treatment device 10 has been used in such a way, cleaning is undertaken to remove extraneous matter from the various units. In this case, the unit, in which the probe unit 14 and the transducer unit 16 are combined, and the outer sheath 150 are separated from the main unit 12 in such an order, for instance, an order opposite to that described above. Particularly, turning the connector 156 allows the connector 156 and the rotation-link member 160 to be unscrewed from each other, thereby permitting the sheath case main part 152 to be pulled together with the connecting member 154 from the insertion member 50. This enables the outer sheath 150 to be easily removed from the insertion member 50.

When cleaning an outer surface of the insertion member 50, the extraneous material, adhered to the operational rod 120, is removed by, for instance, a brush. When this takes place, even if the operational rod 120 is moved forward or rearward or caused to freely move forward or rearward by a force of the brush, the operational rod 120 is sustained under a limited condition available for the limit pin 122 to move forward or rearward only within a predetermined range. This results in the prevention of the operational rod 120 from flexing or bending. Additionally, since the operational rod 120 is exposed to the outside, the extraneous material, adhered to an exterior of the insertion member 50, can be reliably removed by some suitable means such as the brush.

In the meanwhile, when cleaning an inner surface of the insertion member 50 of the main unit 12, that is, an inner peripheral surface of the inner sheath 110, since there is no component part inside the inner sheath 110, cleaning is conducted using the brush or cleaning liquid.

If the main unit of the ultrasonic treatment device is substantially unitarily configured, it takes time in cleaning the operational main member, the inner sheath, the outer sheath and the operational force transfer member. For instance, when removing filths intruded into a space between the inner and outer sheaths, it is hard to allow the brush or the like to enter a narrow space to be brought into direct contact with the filths and not only it takes time but also another need arises for a special cleaning tool.

Further, probabilities may occur wherein only the outer sheath is damaged due to frequent use of the ultrasonic treatment device. In such a case, there is a need for the main unit to be replaced with a new one in its entirety. This is because of the reason that the operational main member, the inner sheath, the outer sheath and the operational force transfer member are substantially unitarily formed with a difficulty caused in disassembling these component parts. Therefore, even if only the outer sheath of the main unit is required for replacement, issues have arisen with an increase in cost for replacement.

On the contrary, the presently filed embodiment has advantageous effects described below.

For instance, even when the outer sheath 150 is damaged, only the outer sheath 150 needs to be removed for replacement and, hence, the outer sheath 150 can be readily replaced with new one, while enabling the suppression of replacement cost to a low value.

For instance, when replacing the main unit 12 upon the occurrence of damage to the main unit 12, replacement cost can be minimized by a value equal to at least that of the outer sheath 150. That is, cost accompanied by replacement of the main unit 12 can be suppressed to the low value.

Since the outer sheath 150 can be removed from the insertion member 50 of the main unit 12, it becomes possible to reliably clean the operational rod 120 in a narrow channel between the outer sheath 150 and the inner sheath 110. For this reason, no special cleaning tool is needed, enabling reduction in cost for cleaning the main unit 12.

As set forth above, the presently filed embodiment is able to provide an ultrasonic treatment device and an ultrasonic treatment apparatus, using such an ultrasonic treatment device, which need no special cleaning tool with the ease of cleaning interiors while an outer sheath can be easily replaced when the occurrence of damage to the outer sheath, covering an ultrasonic probe, is confirmed.

Further, since the base ends of the arms 132*a*, 132*b* of the jaw main part 132 are formed in the arch-like configurations, the arms 132*a*, 132*b* have appropriate strengths even in the formation of thin-wall structures. For this reason, the jaw main part 132 can be formed in a small size.

Since the jaw main part 132 are provided with the projecting portions 132e while the jaw holding member 114 is provided with the protrusions, it becomes possible to prevent stress concentrations, such as increased stresses, from being exerted to, for instance, the coupling pin 140 and the pivot pins 138a, 138b.

In addition, with the presently filed embodiment, as the forward and rearward movement limit mechanism for moving the operational rod 120 along the flat surface portion 116, while description has been made of a structure in which the limit pin 122 and the slit 124 are held in engagement, even in the presence of one or more arch-like limit bands 126 provided on the flat surface portion 116 as shown in FIG. 7C, similar results are obtained. That is, the operational rod 120 extends along the flat surface portion 116 and can be moved under a condition in which the flexing of the operational rod 120 is prevented by the limit band 126.

Second Embodiment

Next, a second embodiment is described with reference to FIGS. 13 and 14. This embodiment is a modified form of the first embodiment and the same component parts as those of the first embodiment bear like reference numerals to omit detail description.

Figure 13:
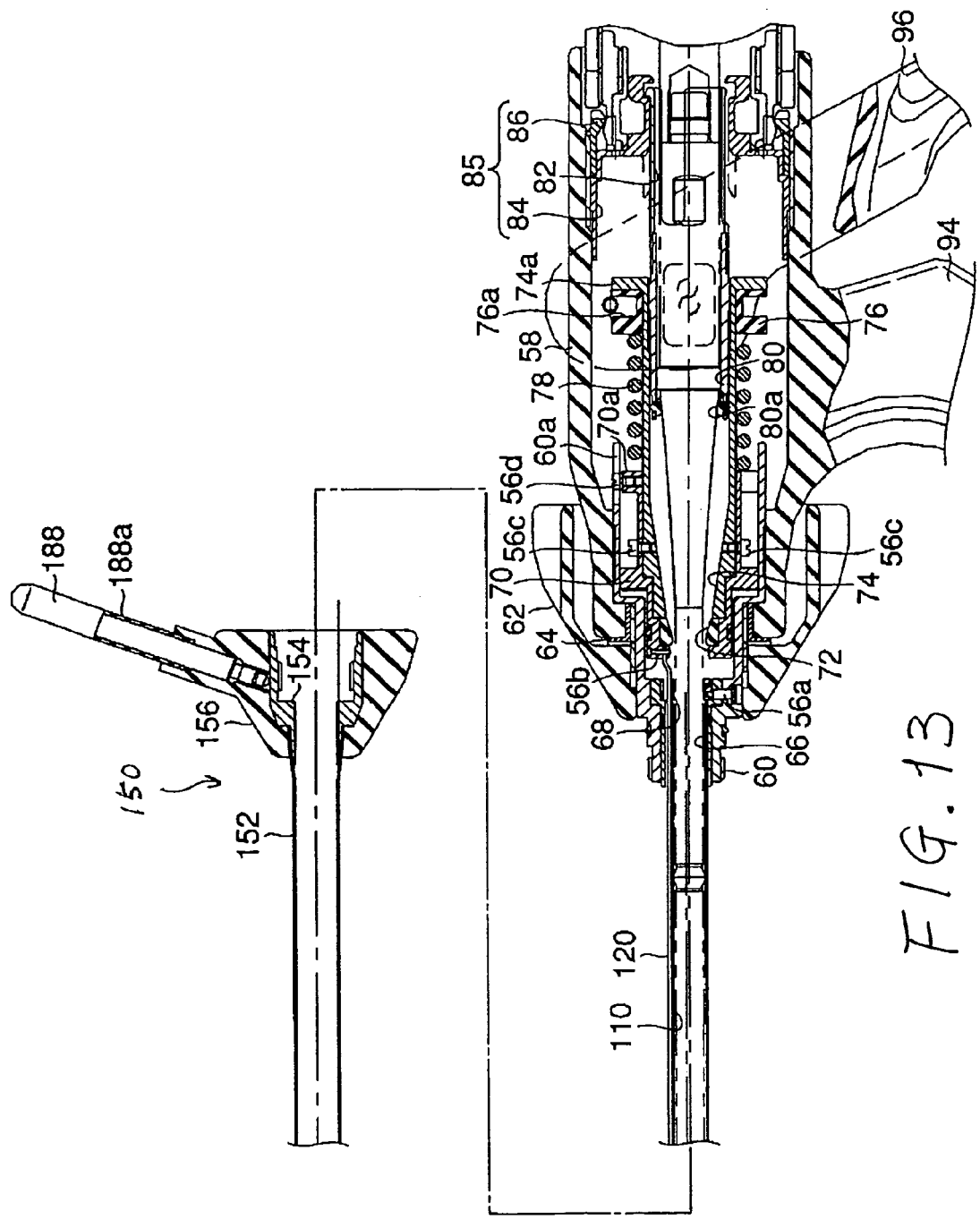
FIG. 13 is a schematic cross sectional view showing a status wherein the outer sheath is inserted from a distal end of the insertion member of the main unit of an ultrasonic treatment apparatus of a second embodiment or the outer sheath is removed from the insertion member of the main unit.
Figure 14:
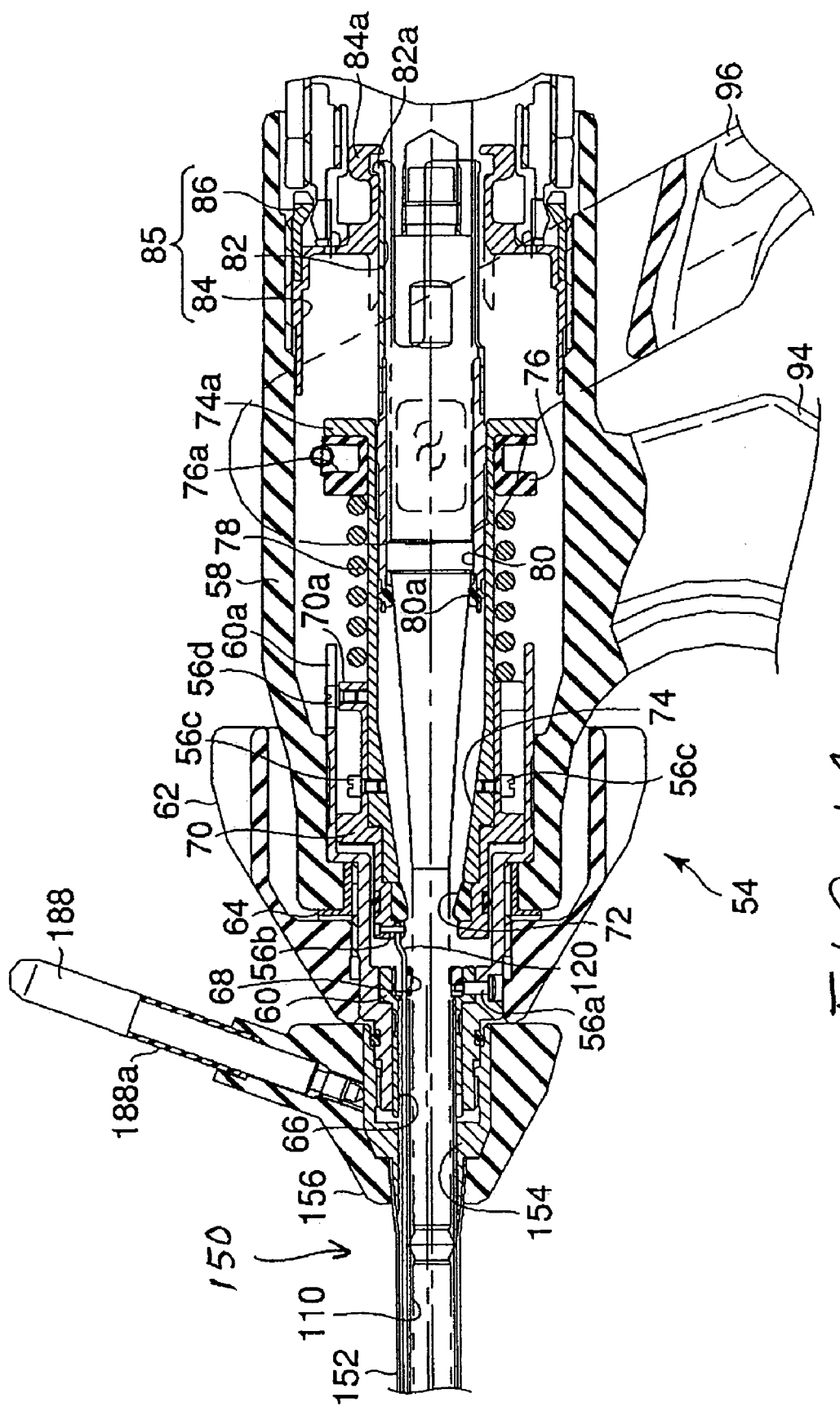
FIG. 14 is a schematic cross sectional showing a status in which the outer sheath is fitted to the insertion member of the main unit of an ultrasonic treatment apparatus of the second embodiment.

As shown in FIG. 13, the high-frequency connector pin 88 is removed from the operational main part 58 of the ultrasonic treatment apparatus 10 of the presently filed embodiment. Instead, a high-frequency connector pin 188 is provided in a connector (electric connector portion) 156 of the outer sheath 150 and covered with an insulative cover 188a. A connector member (electric connector member) 154 of the outer sheath 150 has electrical conductivity.

Therefore, under a situation where the outer sheath 150 is mounted on the outer peripheral surface of the small diameter portion at the distal end of the rotation-link member 60 of the main unit 12, the high-frequency connector pin 188 is electrically connected to the rubber ring 80a via the connecting member 154, the rotation-link member 60, the operational rod connecting member 70, the slider receiving member 74 and the positioning member 80.

Now, operations of the ultrasonic treatment apparatus 10 with such a structure are described.

The treatment member 36 of the probe unit 14, which protrudes from the distal end of the inner sheath 12 of the main unit 12, is inserted to the base end of the outer sheath shown in FIG. 13. Then, the outer sheath 150 is mounted to the main unit 12 as shown in FIG. 14. When this takes place, the outer sheath 150 is rotated relative to the main unit 12 to cause the outer peripheral surface of the small diameter portion of the rotation-link member of the main unit 12 and the inner peripheral surface of the connecting member 154 of the outer sheath 150 to be screwed to each other via respective threads.

Under such a status, if electric current is supplied to the transducer unit 16, ultrasonic treatment can be performed with the treatment device 36.

A high frequency power supply is connected to the high-frequency connector pin 188 located on the outer sheath 150. Under such a condition, a high frequency current is supplied from the high frequency power supply to the high-frequency connector pin 188. Then, the high frequency current is inputted through the rubber ring 80a to the horn part 32 of the probe unit 14 via the high-frequency connector pin 188, the connecting member 154, the rotation-link member 60, the operational rod connecting member 70, the slider receiving member 74 and the positioning member 80. For this reason, if the treatment device 36 of the probe unit 14 is brought into abutment with the living tissue, high frequency treatment can be performed.

Also, no need arises for the high frequency current, flowing through the treatment deice 36 of the probe unit 14 from the high-frequency connector pin 188, to flow through the probe unit 14 as set forth above and the high frequency current may be inputted to the vibration transmitting member 30 and the distal end of the horn part 32 closer to the vibration transmitting member 30. Even in such a case, the high frequency current may be preferably inputted from the node of vibration.

Thus, as the high frequency power supply is connected to the high-frequency connecting pin 188, not only the ultrasonic treatment, which transmits ultrasonic vibration to the probe unit 14, can be performed but also the high frequency treatment, which transmits high frequency current to the probe unit 14, can be implemented on the living tissue.

As set forth above, the presently filed embodiment has advantageous effects described below.

Since the outer sheath 150, which is provided with the high-frequency connecting pin 188, is made detachable, the outer sheath 150 with no high-frequency connecting pin 188 may be used such as when there is no schedule for executing high frequency treatment. Therefore, it becomes easy to achieve switchover between a condition in which the high frequency treatment can be performed and a condition in which no high frequency treatment can be performed upon replacing only the outer sheath 150.

In addition, since only the outer sheath 150 is sufficed for replacement, under circumstances where the high-frequency connecting pin 188, shown in FIG. 4, is provided in the operational main part 58, the main unit 12 can be manufactured in a lower cost than that resulting when the main unit 12 is damaged, making it possible to reduce cost.

Third Embodiment

Next, a third embodiment is described with reference to FIGS. 15 to 18. This embodiment is a modified form of the first embodiment and the same component parts as those described in the first embodiment bear like reference numerals to omit detailed description.

Figure 15:
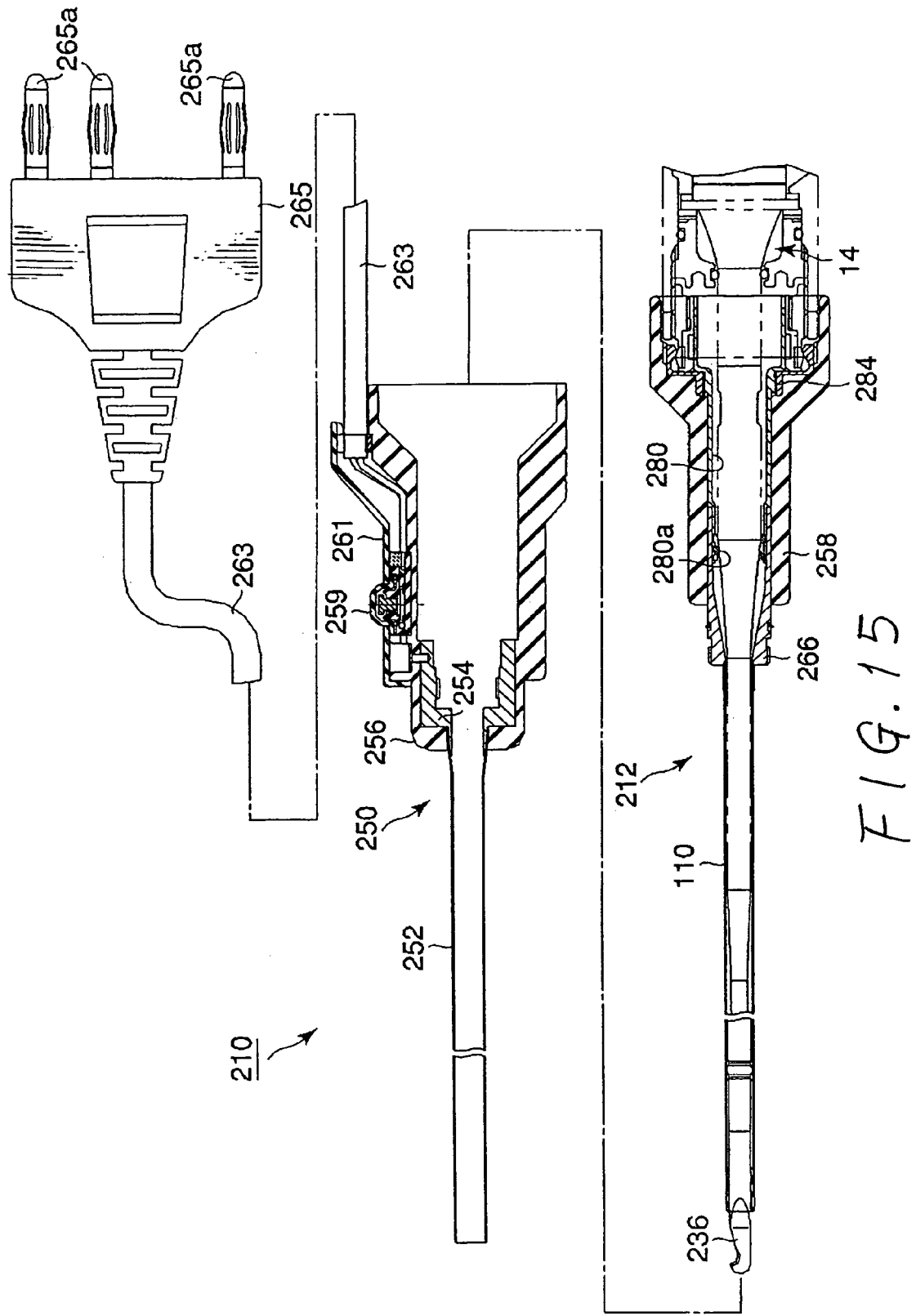
FIG. 15 is a schematic cross-sectional view showing a status wherein a high-frequency sheath unit is inserted from the distal end of the insertion member of the main unit of an ultrasonic treatment apparatus of a third embodiment or the high-frequency sheath unit is removed from the insertion member of the main unit.
Figure 16:
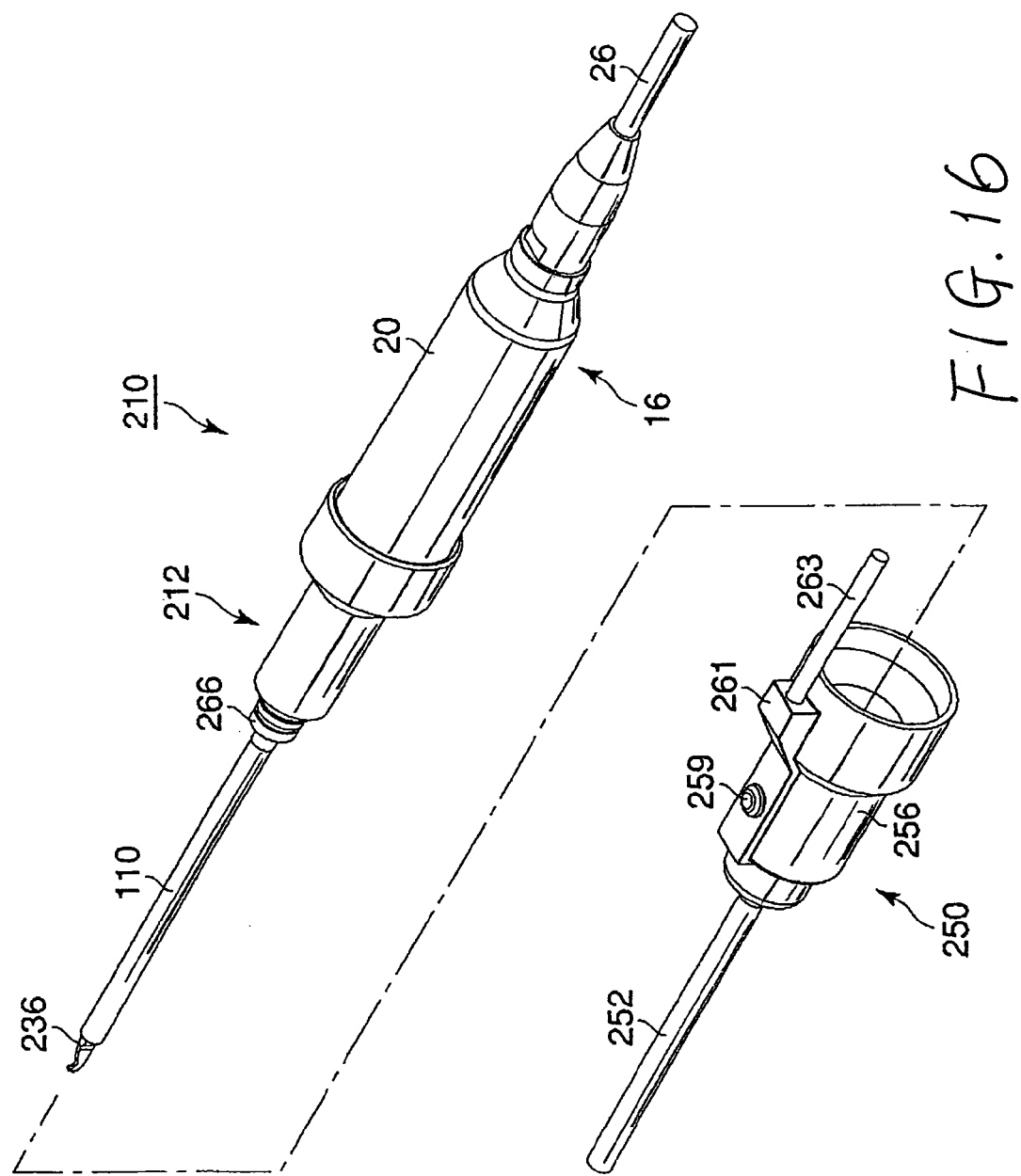
FIG. 16 is a schematic perspective view showing a status wherein a high-frequency sheath unit is inserted from the distal end of the insertion member of the main unit of an ultrasonic treatment apparatus of a third embodiment or the high-frequency sheath unit is removed from the insertion member of the main unit.

As shown in FIG. 15, an ultrasonic treatment apparatus 210 of the presently filed embodiment is comprised of a main unit 212, a probe unit 14 and a transducer unit 16 (see FIG. 16). The main unit 212 further includes a high-frequency sheath unit (outer sheath) 250 that is detachably mounted to the insertion member 50 of the main unit 12.

The main unit 212 is comprised of an operational main member 258, a sheath connecting member 266, a positioning member 280 and a transducer unit guide 284. The operational main member 258 is formed in a tubular shape with insulation property. The operational main member 258 has a distal end with its inner peripheral surface to which the sheath connecting member 266, to which the base end of the inner sheath is connected, is connected. The sheath connecting member 266 has a distal end that protrudes beyond the distal end of the operational main member 258. An outer peripheral surface of the distal end of the sheath connecting member 266 is formed with a male threaded portion.

The sheath connecting member 266 has a base end to which a distal end of the positioning member 280 is fitted in abutting engagement with an inner peripheral surface of the operational main member 258. The positioning member 280 has the distal end that has an inner peripheral surface on which a rubber ring (electric connecting part) with electric conductivity is located. The positioning member has the base end that has an outer peripheral surface provided with the transducer unit guide 284. The positioning member 280 and the guide 284 form a transducer connecting member. Also, the distal-end operating member 52 is removed from the distal end of the inner sheath 110.

The high-frequency sheath unit 250 is comprised of a sheath main part 252, a connecting member 254 and a connector 256. The sheath main part 252 and the connector 256 have insulation properties and the connecting member 254 has electric conductivity. The connector 256 has an inner peripheral surface formed with a female threaded portion that can be screwed onto a male threaded portion on an outer peripheral surface of the sheath connecting member 266. The connector 256 has an outer peripheral surface on which a push-switch 259 is mounted. The switch 259 has a periphery covered with an insulative cover 261. One end of a chord 263, connected to the switch 259, is fixedly mounted between the connector 256 and the insulative cover 261. The chord 263 has the other end on which a connector-pin-use connector 265 is mounted. With such a structure, as the push-switch 259 is depressed, electrical connection is established between a connector pin 265a of the connector-pin connector 265 and the connecting member 254 via the chord 263. If the push-switch 259 is released, the connector pin 265a of the connector-pin connector 265 and the connecting member 254 are electrically disconnected from each other.

The probe unit 14 includes a treatment device (curved member) 236 formed in a hook-shape.

Now, operations of the ultrasonic treatment apparatus 210 with such a structure are described.

Figure 17:
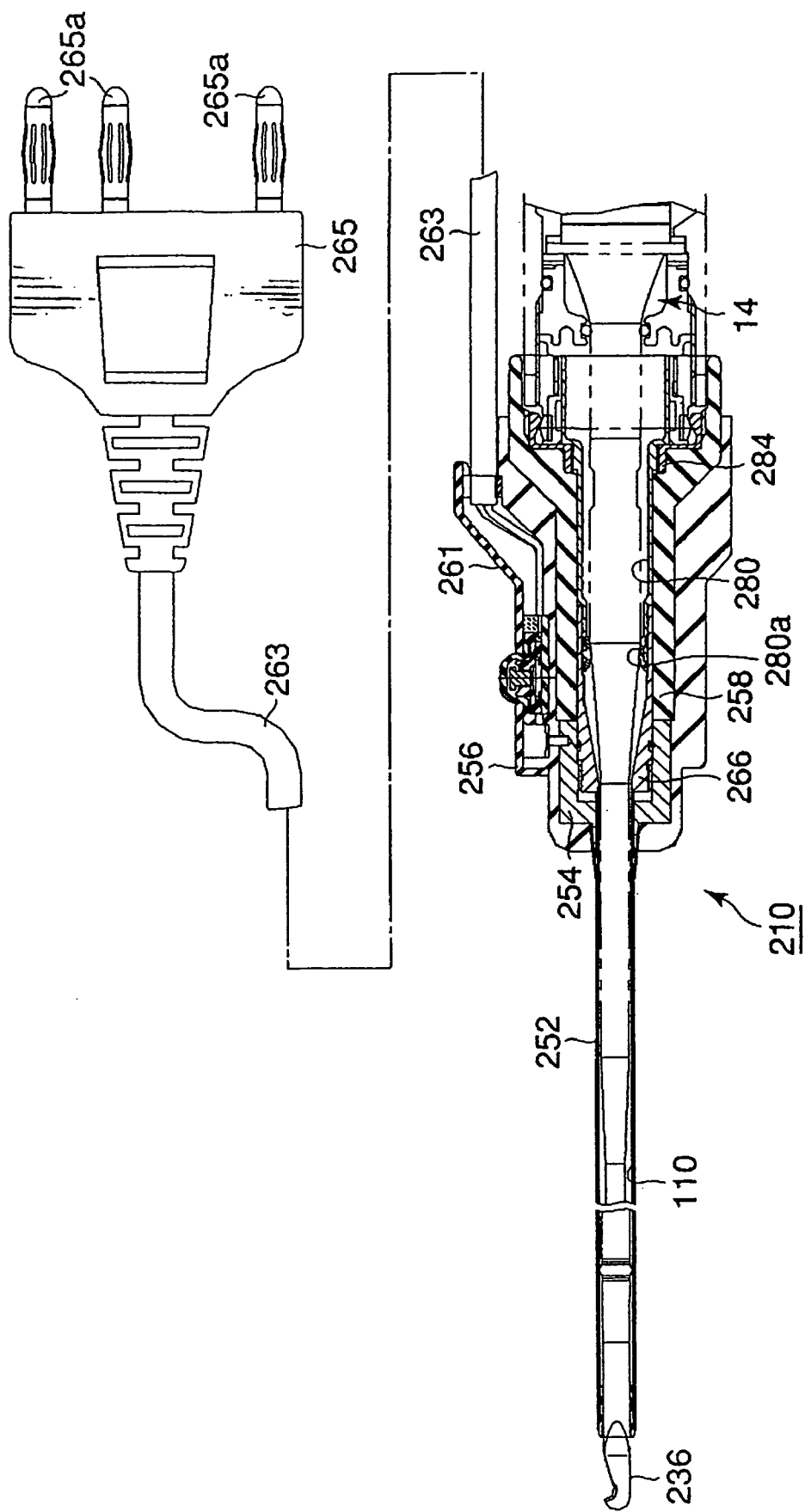
FIG. 17 is a schematic cross-sectional view showing a status wherein the high-frequency sheath unit is fitted to the insertion member of the main unit of an ultrasonic treatment apparatus of the third embodiment.
Figure 18:
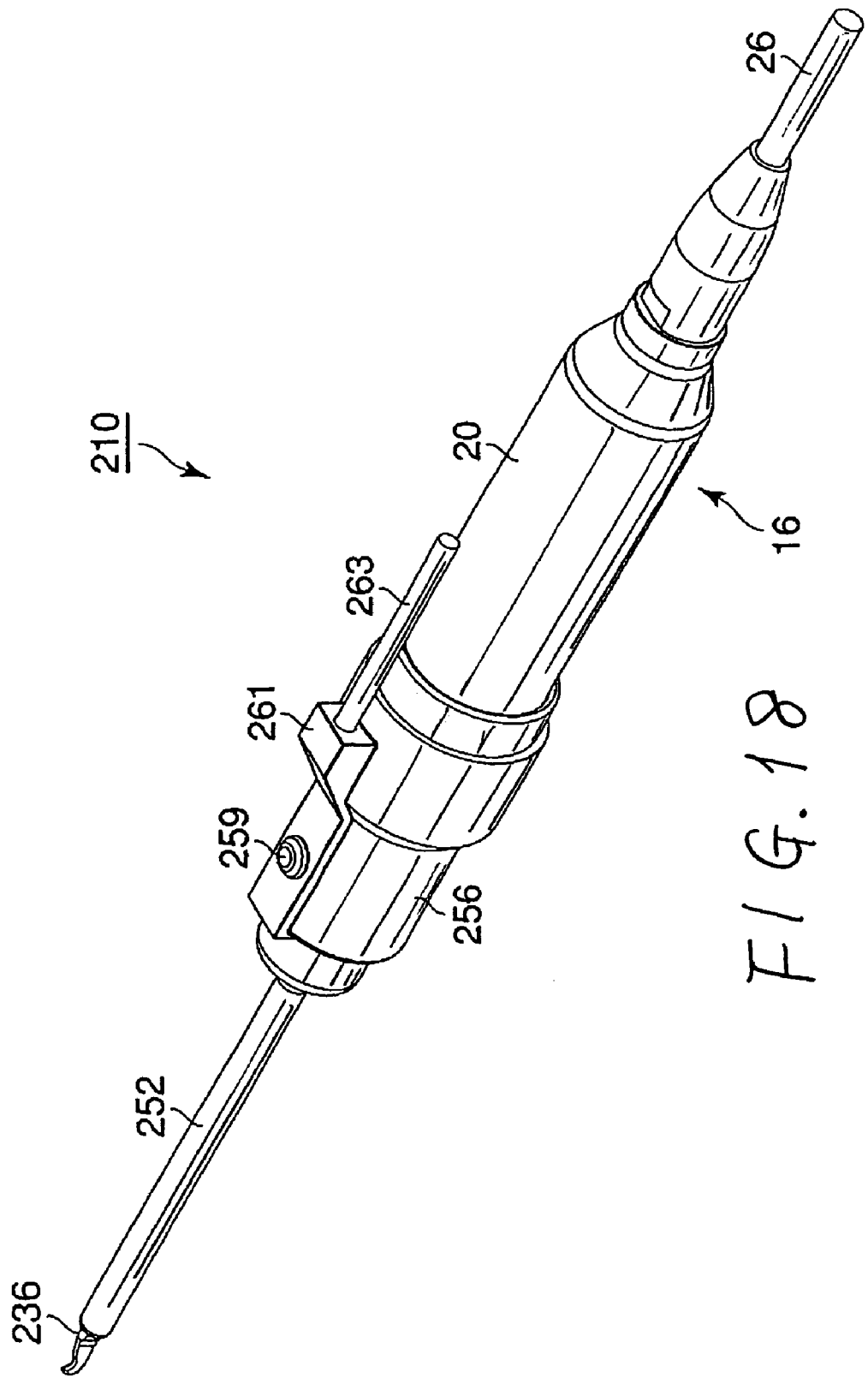
FIG. 18 is a perspective view showing a status wherein the high-frequency sheath unit is fitted to the insertion member of the main unit of an ultrasonic treatment apparatus of the third embodiment.

The treatment device 236 of the probe unit 14, protruding from the distal end of the inner sheath 110 of the main unit 12, is inserted to the base end of the high-frequency sheath unit 250 as shown in FIGS. 15 and 16. Then, as shown in FIGS. 17 and 18, the high-frequency sheath unit 250 is mounted to the main unit 212 as shown in FIGS. 17 and 18. When this takes place, rotating the main unit 212 with respect to the high-frequency sheath unit 250 allows the sheath connecting member 266 of the main unit 212 and the connecting member 254 of the high-frequency sheath unit 250 to be screwed to each other via the respective threads.

Under such a condition, upon supply of electric current to the transducer unit 16, ultrasonic treatment can be performed with the treatment device 236.

A high frequency power supply is connected to the connector pin 265a mounted on the high-frequency sheath unit 250. Under such a status, high frequency current is supplied from the high frequency power supply and the push-switch 259 is depressed. Then, the high frequency current is applied to the horn part of the probe unit 14. Therefore, when the living tissue is brought into contact with the treatment member 236 of the probe unit 14, high frequency treatment is performed.

As set forth above, the presently filed embodiment has advantageous effects described below.

Since the high-frequency sheath unit 250 is made detachable relative to the main unit 212, the ultrasonic treatment apparatus 210 may be used only as an ultrasonic treatment apparatus without mounting the high-frequency sheath unit 250 under situations where no schedule exists for high frequency treatment. Therefore, it becomes easy to achieve switchover between a condition in which the high frequency treatment can be performed and a condition in which no high frequency treatment is performed upon detachably mounting the high-frequency sheath unit 250.

The various embodiments, set forth above, are configured in a manner described above. Therefore, to sum up advantageous effects in contrast to those of the present invention, the advantageous effects are listed as follows.

First, it becomes possible to provide an ultrasonic treatment device and an ultrasonic treatment apparatus using such as an ultrasonic treatment that provides the ease of cleaning interiors of associated component parts with no need for preparing a special cleaning device while making it easy to replace an outer sheath when the occurrence of damage to the outer sheath, by which an ultrasonic probe is covered, is confirmed.

More particularly, since the outer sheath can be removed from the apparatus main part and the main unit, component parts, incorporated inside the outer sheath, can be easily cleaned and, even in the occurrence of damage to the outer sheath, replacing only the outer sheath enables the ultrasonic treatment apparatus to be reused. Further, even when the occurrence of damage to the apparatus main part and the main unit is confirmed, it becomes possible to achieve reduction in cost for replacements of the apparatus main part and the main unit by a value equivalent to the cost of the outer sheath.

Further, the inner sheath is possible to include the forward and rearward movement limit mechanism that precludes the forward and rearward direction of the operational force transfer member from being deviated from a direction along the axial direction of the inner sheath. Thus, the movement of the operational force transfer member is restricted during a period when the operational force transfer member is moved forward or rearward, under a condition where the outer sheath is removed, and cleaning is performed using a brush. This result in the prevention of the operational force transfer member from being largely flexed and the operational force transfer member is prevented from damage.

Furthermore, the operational force transfer member has the plate-like configuration formed with the slit portion along the axial direction of the operational force transfer member. The forward and rearward movement limit mechanism is able to incorporate the limit pin associated with the slit portion to prevent the forward and rearward movements of the operational force transfer member from being deviated from the direction along the axial direction of the inner sheath. This enables the limit pin to prevent the operational force transfer member from being deviated from the direction along the axial direction of the inner sheath.

Moreover, the forward and rearward movement limit mechanism is possible to include the limit band disposed around the outer periphery of the inner sheath to limit the movement of the operational force transfer member in a direction intersecting the axial direction thereof. Therefore, the operational force transfer member can be prevented from deviated from the direction along the axial direction of the inner sheath.

In addition, the operational force transfer member may include a plate-like member that is movable forward or rearward along the axial direction of the inner sheath. This results in a capability of locating the operational force transfer member in a further narrow space and the forward and rearward movement limit mechanism enables the operational force transfer member to be prevented from being deviated from the direction along the axial direction of the inner sheath.

Besides, the outer sheath is comprised of the insulation sheath with insulation property by which the outer periphery of the ultrasonic probe is covered in the fitted status, the electric connector member, disposed in the base end of the insulation sheath to enable switchover between the mount position and an escape position relative to the apparatus main part, which is electrically connected to the power supply for the electric cautery, and the electrical connecting member, electrically connected to the electric connector member, which is electrically conduct the ultrasonic probe when the electric connector member is placed in the fitted status.

Thus, for instance, when a need arises for the high frequency treatment to be performed, mounting the outer sheath, with such a structure, onto the ultrasonic treatment apparatus enables high frequency current to flow through the ultrasonic probe. That is, when there is no need for performing the high frequency treatment, mere the outer sheath may be detachably mounted to the ultrasonic treatment apparatus and the operator is possible to select the outer sheath to provide a capability of selectively perform the high frequency treatment.

Further, the electric connecting member is brought into abutment with the position at which there is provided the node of the vibration on the ultrasonic probe under a status where the electrical connecting member is placed on the operational main member in the fitted status. Therefore, even in cases where the ultrasonic probe is applied with not only the high frequency current but also the ultrasonic vibration, mutually related adverse affects can be minimized.

In the foregoing, while the several embodiments have been described above in detail with reference to the accompanying drawings, the present invention is not limited to such embodiments set forth above and all embodiments may be implemented within a range without departing from the scope of the present invention.

What is claimed is:

1. An ultrasonic treatment device comprising:
   a transducer unit equipped with an ultrasonic transducer generating ultrasonic vibration in response to supply of power;
   a probe unit configured to have a treatment member at a distal end thereof, detachably loaded to the transducer unit, and equipped with an ultrasonic probe transmitting the ultrasonic vibration to the distal end of the treatment member when the transducer unit is loaded to the probe unit;
   a main unit which is adapted to be manually grasped by an operator, to which the probe unit with the transducer unit loaded thereto is detachably loaded, and which has a cylindrical insert through which the ultrasonic probe is inserted and positioned within, to have the treatment member protruded outwardly when the probe unit is loaded and an outer sheath detachably covering an outer surface of the insert;
   an electric connector disposed at a base end of the outer sheath and electrically connected to a power source for electric cautery; and
   an electric connecting portion connected to the electric connector and configured to allow the electric connector to be connected electrically to the ultrasonic probe when the outer sheath is loaded to the main unit; and wherein the electric connecting portion is located to contact a portion of the ultrasonic probe at a node of vibration thereof, when the outer sheath is loaded into the main unit.

2. The device according to claim 1, wherein the outer sheath is provided with a cylindrical sheath body and a connector detachably connecting the cylindrical sheath body to the main unit.

3. The device according to claim 2, wherein an inner diameter of the cylindrical sheath body is larger than an outer diameter of the insert, whereby the ultrasonic probe of the probe unit with the transducer unit loaded thereto are insertable into the cylindrical sheath body.

4. The device according to claim 1, wherein the treatment member of the ultrasonic probe comprises a curved portion bent to deviate from an axial direction of the ultrasonic probe.

5. The device according to claim 4, wherein the curved portion comprises a hook portion bent to deviate from the axial direction and is able to hook a target to be treated.

6. The device according to claim 1, wherein the main unit comprises an operation member to which the probe unit with the transducer unit loaded thereto is detachable and which is adapted to be grasped by the operator,
   a cylindrical inner sheath providing part of the insert,
   a jaw rotatably supported to face the treatment member of the ultrasonic probe at a distal end of the inner sheath and adapted to grip living tissue of the subject together with the treatment member, and
   an operational force transfer member linking the jaw and the operation member, and configured to move forward and backward along an axial direction of the inner sheath, and to transmit to the jaw an operation force generated by the operation member.

7. An ultrasonic treatment device comprising:
   a main unit having an operation member adapted to be grasped and operated by an operator;
   an ultrasonic transducer;
   a treatment member;
   an ultrasonic probe detachably loaded to the main unit and configured to transmit ultrasonic vibration generated by the ultrasonic transducer to the treatment member, the ultrasonic transducer being located at a base end of the probe and the treatment member being located at a distal end of the probe;
   an inner sheath approximately cylindrically shaped, arranged in the main unit, and configured to allow the ultrasonic probe to be inserted therethrough and positioned within, when the ultrasonic probe is loaded to the main unit;
   a jaw rotatably supported to face the treatment member of the ultrasonic probe at a distal end of the inner sheath when the ultrasonic probe is loaded to the main unit and formed to grip living tissue of the subject together with the treatment member;
   an operational force transfer member linking the jaw and the operation member, and configured to move forward and backward on a surface of the inner sheath along an axial direction of the inner sheath, and to transmit to the jaw an operation force generated by the operation member;
   an outer sheath detachably attached to the main unit to cover an outer surface of the inner sheath and the operational force transfer member; and
   an electric connector disposed at a base end of the outer sheath and electrically connected to a power source for electric cautery.

8. The device according to claim 7, wherein the outer sheath is provided with a cylindrical sheath body and a connector detachably connecting the cylindrical sheath body to the main unit.

9. The device according to claim 8, wherein the inner sheath comprises a back-and-forth movement limiting mechanism preventing the operational force transfer member from moving back and forth along a direction deviating from an axial direction of the inner sheath.

10. The device according to claim 9, wherein
   the operational force transfer member comprises a plate-like slit portion formed along an axial direction of the operational force transfer member and the back-and-forth movement limiting mechanism comprises a limit pin arranged in the slit portion and formed to prevent the operational force transfer member from moving back and forth along the direction deviating from the axial direction of the inner sheath.

11. The device according to claim 9, wherein the back-and-forth movement limiting mechanism comprises a limit band arranged on an outer face of the inner sheath and configured to limit the operational force transfer member from moving in a direction perpendicular to an axial direction of the operational force transfer member.

12. The device according to claim 11, wherein the operational force transfer member comprises a plate-like member movable back and forth along the axial direction of the inner sheath.

13. The device according to claim 7, wherein the outer sheath is provided with
an electric connecting portion connected to the electric connector and configured to allow the electric connector to be connected electrically to the ultrasonic probe when the outer sheath is loaded to the main unit.

14. The device according to claim 13, wherein the electric connecting portion is located to contact a portion of the ultrasonic probe at a node of vibration thereof, when the outer sheath is loaded to the main unit.

15. An ultrasonic treatment device comprising:
a main unit adapted to be grasped and operated by an operator; and
a probe unit detachably loaded to the main unit and formed to transmit ultrasonic vibration from a base end of the probe unit to a distal end of the probe unit, the ultrasonic vibration being generated by an ultrasonic transducer and a treatment member being disposed at the distal end of the probe unit,
wherein the main unit comprises
an inner sheath through which the probe is inserted and positioned within, when the probe unit is loaded to the main unit,
a jaw rotatably supported to face the treatment member at a distal end of the inner sheath and formed to grip living tissue of the subject together with the treatment member,
an operation member disposed at a base end of the inner sheath and adapted to be operated by the operator,
an operational force transfer member linking the jaw and the operation member, and configured to move forward and backward on a surface of the inner sheath along an axial direction of the inner sheath, and to transmit to the jaw an operation force generated by the operation member;
an outer sheath detachably attached to the main unit to cover an outer surface of the inner sheath,
an electric connector disposed at a base end of the outer sheath and electrically connected to a power source for electric cautery,
an electric connecting portion connected to the electric connector and configured to allow the electric connector to be connected electrically to the ultrasonic probe when the outer sheath is loaded to the main unit, and
the electric connecting portion being configured to contact a portion of the ultrasonic probe at a node of vibration thereof, when the outer sheath is loaded to the main unit.

16. The device according to claim 15, wherein the outer sheath is provided with a cylindrical sheath body and a connector detachably connecting the cylindrical sheath body to the main unit.

17. A treatment apparatus comprising:
a probe comprising an energy transmitting member and a treatment member and being configured to enable physical energy to be transmitted to the treatment member through the energy transmitting member to allow the treatment member to medically treat living tissue of a subject to be treated;
a device movably supported near to the treatment member by the probe and formed to be in charge of a cooperative operation for the living tissue together with the probe;
an operation member operable to move the device from or toward the treatment member;
a first sheath which links the device and the operation member and through which the energy transmitting member is inserted and positioned within;
an operational force transfer member linking the device and the operation member, movably disposed along an outer surface of the first sheath, and effective to transmit an operation force from the operation member to the device;
a second sheath detachably loaded to the operation member to cover the first sheath as well as the operation force transfer member,
an electric connector disposed at a base end of the second sheath and electrically connected to a power source for electric cautery,
an electric connecting portion connected to the electric connector and configured to allow the electric connector to be connected electrically to the probe when the second sheath is loaded, and
the electric connecting portion being configured to contact a portion of the energy transmitting member at a node of vibration thereof, when the second sheath is loaded.

18. The treatment apparatus according to claim 17, wherein
the physical energy is ultrasonic vibration energy,
the probe is an ultrasonic probe,
the device is a jaw supported to face the treatment member, and configured to open and close from and toward the treatment member, and to grip living tissue of the subject together with the ultrasonic probe, and
the operation member is configured to control opening and closing the jaw from and toward the treatment member.

* * * * *